United States Patent [19]
Olson et al.

[11] Patent Number: 6,088,616
[45] Date of Patent: Jul. 11, 2000

[54] FIELD PROGRAMMABLE AUTOMATED EXTERNAL DEFIBRILLATOR

[75] Inventors: Kenneth F. Olson, Edina; William S. Parker, Maple Grove; Michael A. Tvedt, Savage, all of Minn.

[73] Assignee: SurVivaLink Corporation, Minneapolis, Minn.

[21] Appl. No.: 09/057,043

[22] Filed: Apr. 8, 1998

Related U.S. Application Data

[60] Provisional application No. 60/043,885, Apr. 10, 1997.

[51] Int. Cl.$^7$ ........................................... A61N 1/39
[52] U.S. Cl. ................................. 607/5; 607/59
[58] Field of Search ..................... 607/5, 59, 30

[56] References Cited

U.S. PATENT DOCUMENTS

| | | |
|---|---|---|
| 4,295,474 | 10/1981 | Fischell . |
| 4,628,935 | 12/1986 | Jones et al. . |
| 5,002,062 | 3/1991 | Suzuki ................................. 600/523 |
| 5,285,781 | 2/1994 | Brodard ................................. 607/66 |
| 5,607,454 | 3/1997 | Cameron et al. ......................... 607/6 |
| 5,697,960 | 12/1997 | Molin et al. ............................ 607/59 |
| 5,716,380 | 2/1998 | Yerkovich et al. . |
| 5,755,745 | 5/1998 | McGraw et al. ......................... 607/59 |
| 5,836,993 | 11/1998 | Cole ...................................... 607/59 |

*Primary Examiner*—Kennedy Schaetzle
*Attorney, Agent, or Firm*—Patterson & Keough, P.A.

[57] ABSTRACT

An automated external programmable defibrillator (AED) with the ability to perform operational self-tests, determine whether a patient is undergoing cardial defibrillation, deliver an electrical defibrillation pulse, store data pertaining to the self-tests. Certain operational parameters are alterable by software installable in a computer. The operational parameters include second defibrillation shock energy value, the maximum shocks to be delivered during a rescue, whether the same energy will be delivered to the patient upon conversion to a shockable rhythm, whether the AED will automatically convert to daylight savings time, whether an electrode test will occur during the self-test, and whether ambient sound will be recorded during a rescue.

21 Claims, 21 Drawing Sheets

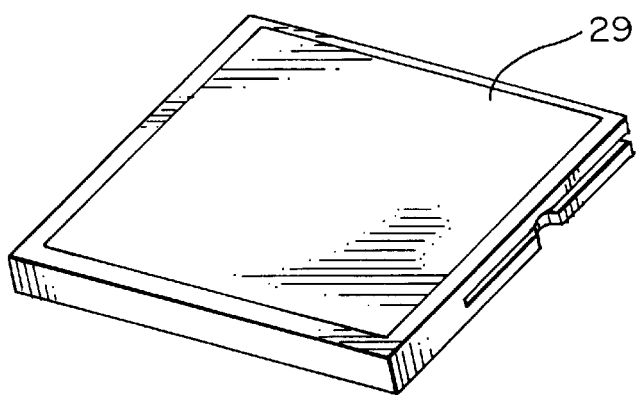
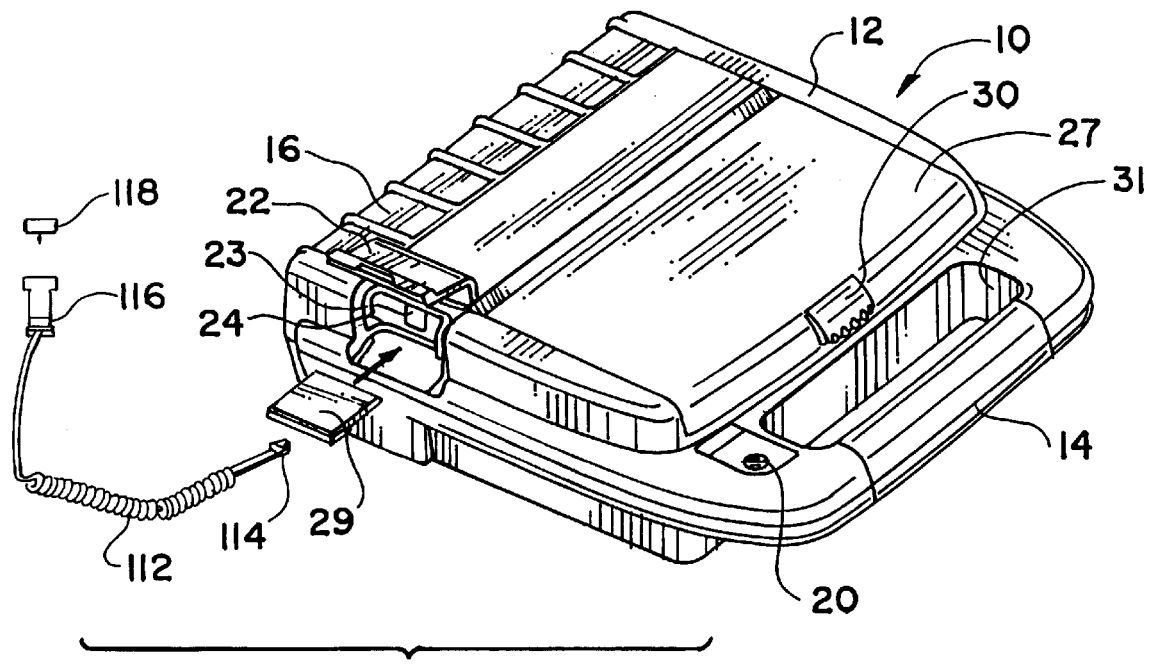

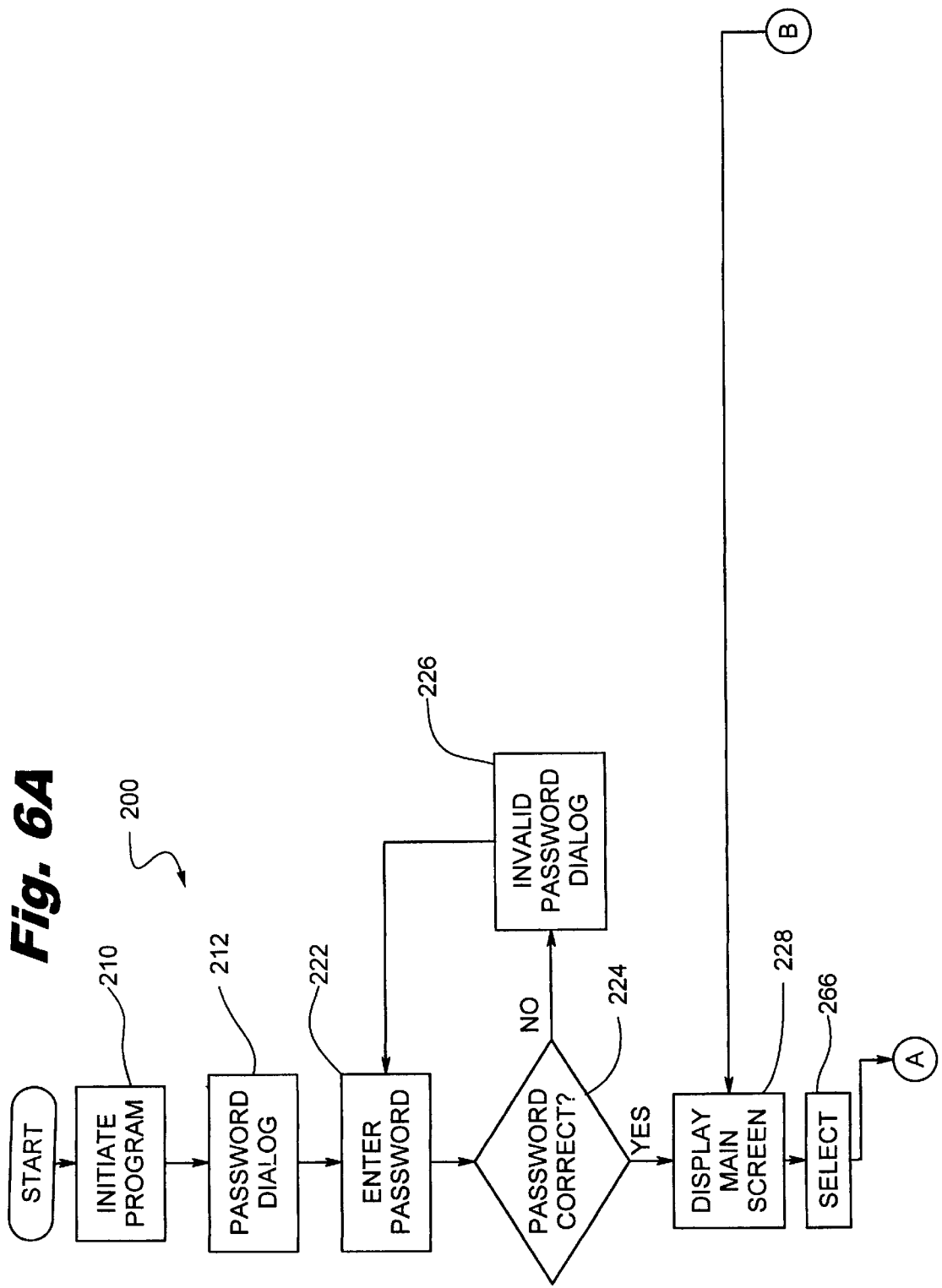

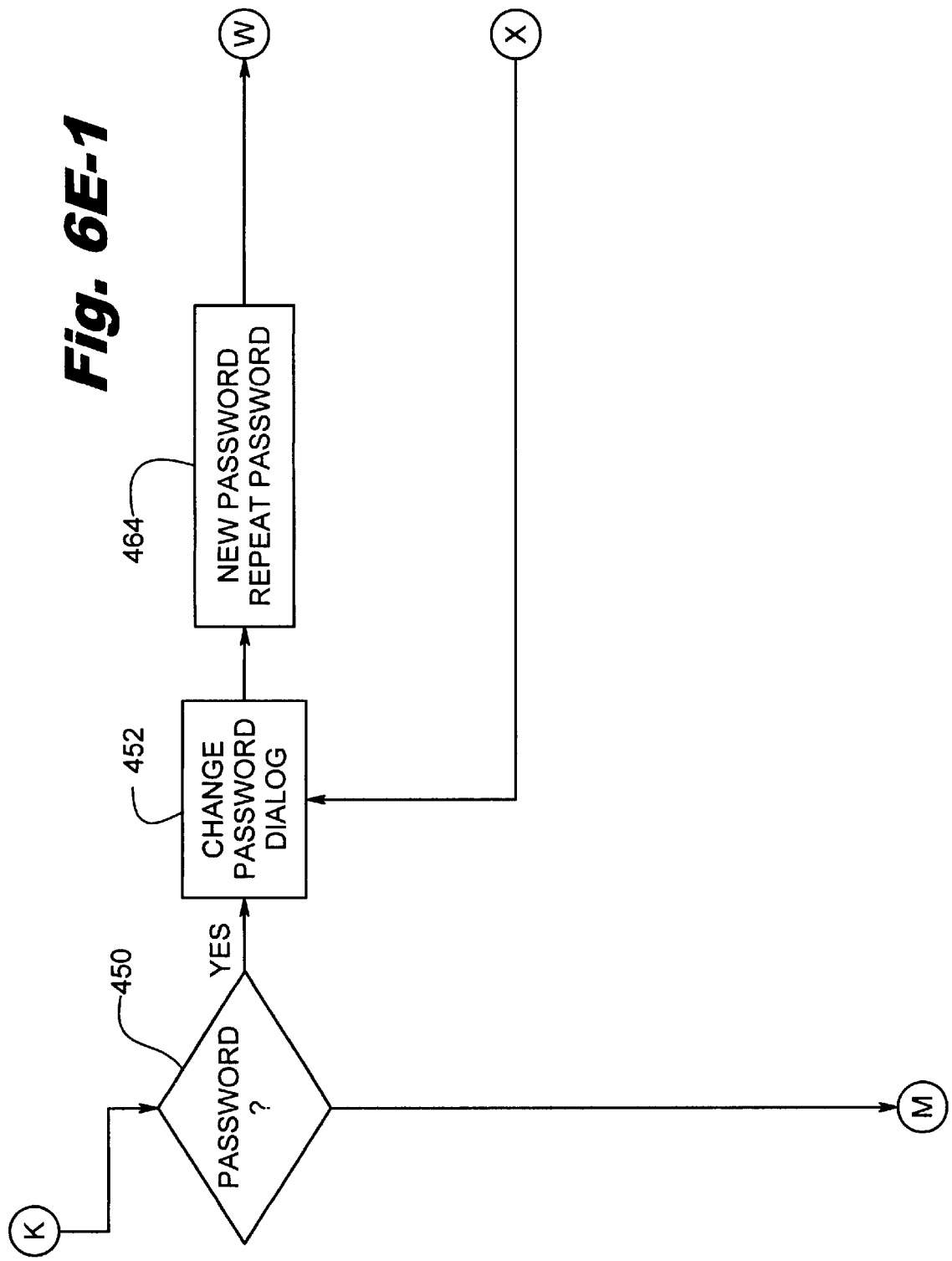

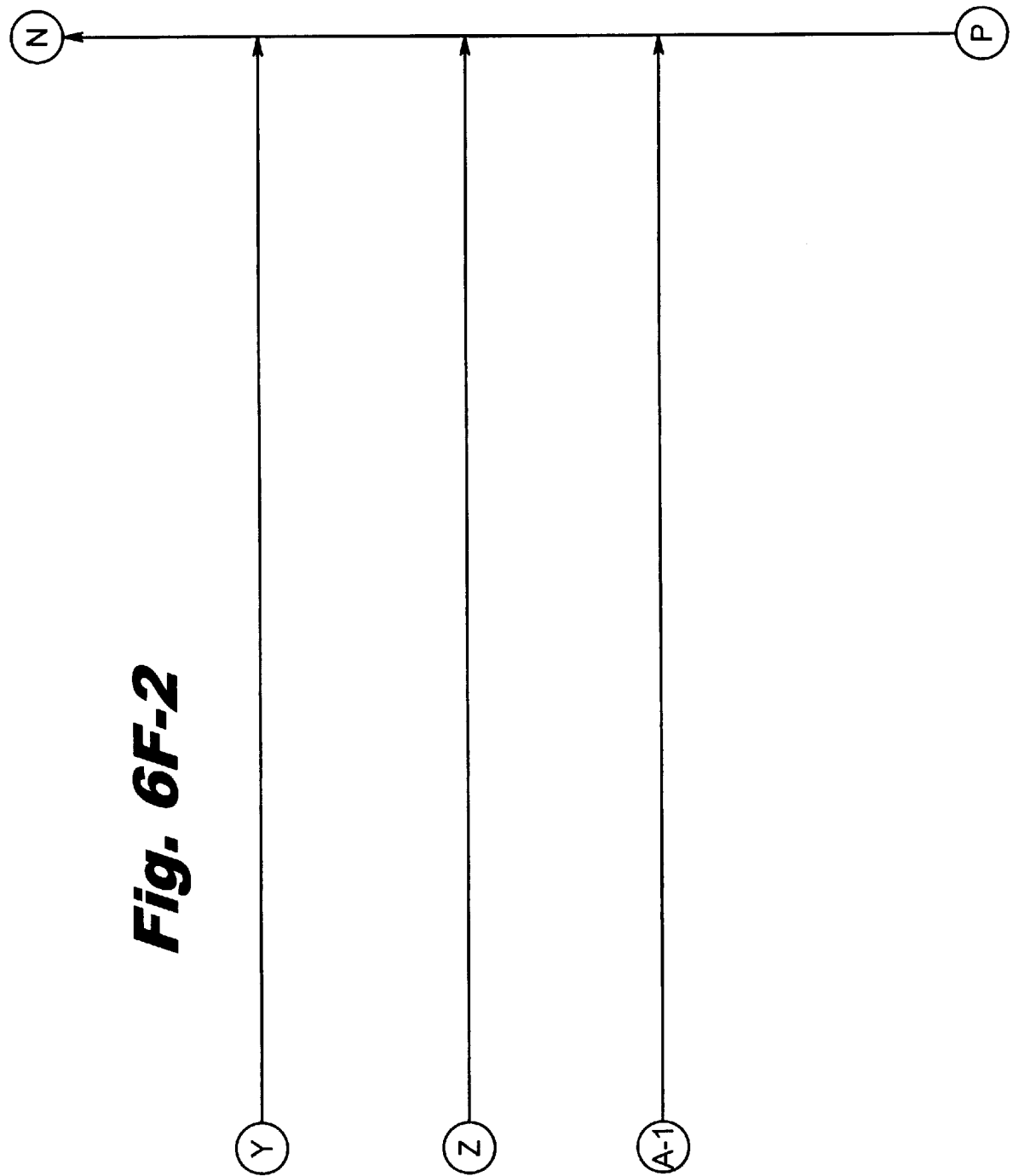

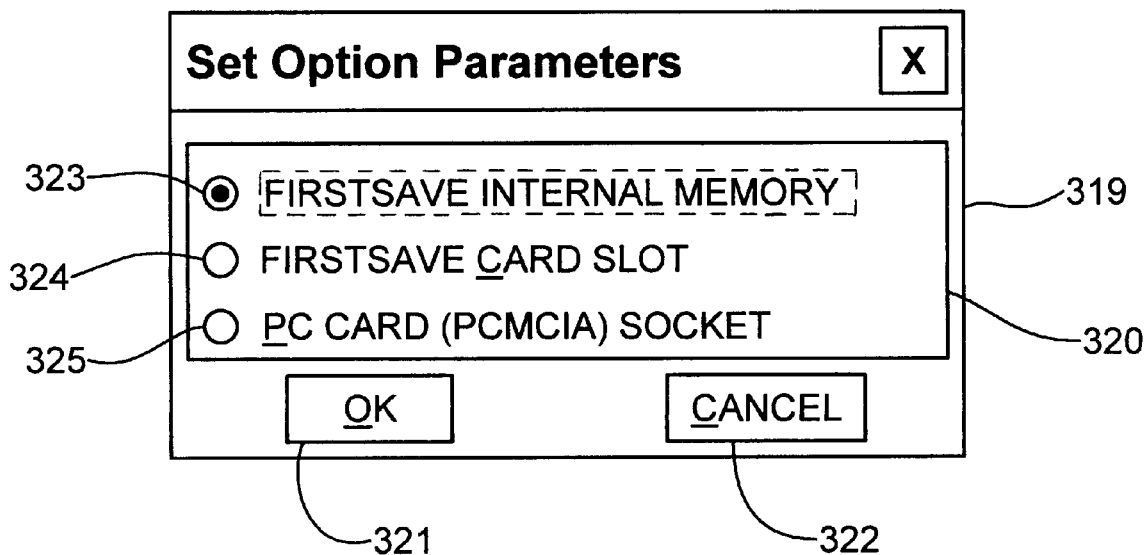

FIELD PROGRAMMABLE AUTOMATED EXTERNAL DEFIBRILLATOR

CROSS-REFERENCES TO RELATED APPLICATIONS

This application claims the benefit of U.S. Provisional application No. 60/043,885, filed Apr. 10, 1997, the contents of which are incorporated herein by reference and priority to which is claimed by 35 U.S.C. § 119(e).

FIELD OF THE INVENTION

The present invention relates generally to automated external defibrillators. In particular, the present invention is an automated external defibrillator (AED) and a method in which operating parameters may be selectively altered.

BACKGROUND OF THE INVENTION

Automated external defibrillators (AEDs) are used by police officers, paramedics and other first-responder emergency medical technicians to resuscitate patients undergoing cardiac arrest. It is important that the AEDs carried by these technicians be continuously operational and ready for use on a moment's notice. It is essential that the technician be able to rely on the operability of the AED when responding to a cardiac arrest. Studies have shown that the chances of successfully resuscitating a patient decreases approximately ten percent per minute following cardiac arrest. Thus, it is vital to be able track and monitor the operation of the AED and its operators through various rescue events so that appropriate and timely responses by the AED and its operators may be ensured.

In the U.S., protocol guidelines for amplitude, duration, and the number of defibrillation shocks or pulses administered are provided by such organizations as the American Heart Association. However, protocol operating requirements may differ among locations inside and outside the U.S.

There is, therefore, a need for an AED with the capability for at least some of these operational parameters to be altered to meet specific requirements of a plurality of countries and organizations which have differing rescue protocols. There is a further need for an AED with the ability to record rescue information including patient data and the sound from a rescue event and to execute certain self-tests to ensure readiness for a rescue. Such alterations should be capable of being performed locally in the field after the AED has been delivered to the end user.

SUMMARY OF THE INVENTION

The present invention substantially meets the aforementioned needs of the industry by providing a parameter altering capability. These alterations may be performed locally in the field without recourse to factory assistance. In a preferred embodiment, the AED operating parameter value may be selected from a group comprising: a subsequent defibrillation shock energy value, a maximum number of defibrillation shocks deliverable during a rescue, a defibrillation shock energy value subsequent to a defibrillation conversion of the patient's heart, an automatic adjustment of an AED time clock to daylight savings time, whether an electrode test will be administered during the self-test, and whether ambient sound will be recorded during a rescue.

The present invention is an automated external defibrillator (AED) for performing a rescue intervention on a patient. The AED has a case for housing a power supply, the power supply powering a microprocessor. The power supply and the microprocessor are electrically connected to a circuit for generating a defibrillation shock. The circuit is electrically connected to a pair of electrodes that are applied to the patient to control and to deliver the defibrillation shock to the patient. The microprocessor has a circuitry to store at least one operating parameter. The AED includes apparatus for altering at least one AED operating parameter value in the field, the operating parameter value being programmed in the microprocessor. The apparatus for altering is an information storage medium disposed operationally exterior to said case and that is selectively communicatively coupled to the microprocessor.

The invention further includes a method of monitoring and altering an operating parameter of an automated external defibrillator (AED) in the field that include the steps of:

communicatively coupling an information storage medium to the microprocessor of the AED in the field, the information storage medium being disposed operationally exterior to said case and being selectively communicatively couplable to the microprocessor of the AED;

initiating a program installed in the information storage medium;

monitoring the operating parameter stored in a microprocessor program; and altering the operating parameter as desired.

BRIEF DESCRIPTION OF THE DRAWINGS

FIG. 3 is a perspective view of a rescue information data card;

FIG. 4 is a perspective view of the AED having the rescue information data card being inserted therein according to the present invention;

FIGS. 6A–6G represent a flow chart depicting the logic flow of the software of the present invention;

FIG. 16 depicts the Set Option Parameters Screen Display generated by the program of the present invention.

DETAILED DESCRIPTION OF THE DRAWINGS

Figure 1:
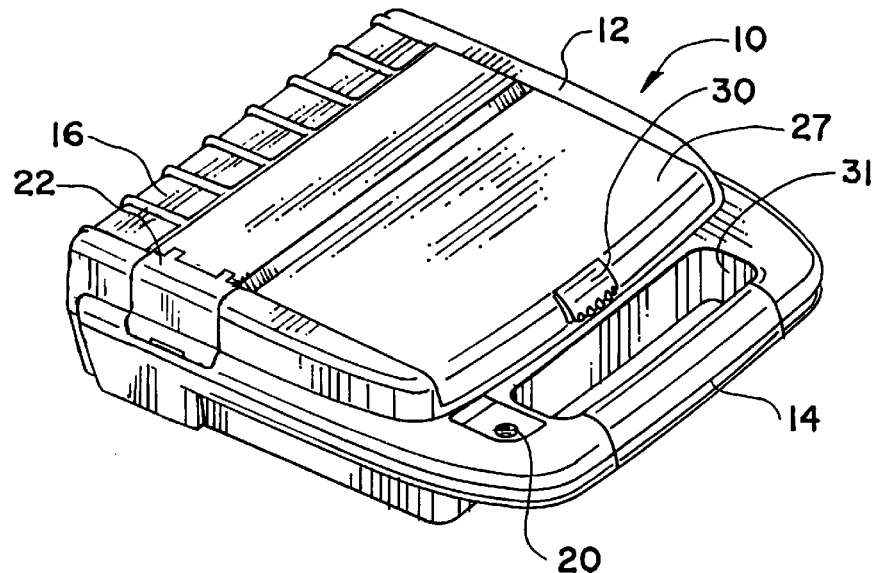
FIG. 1 is a perspective view of an automated external defibrillator (AED)

The AED of the present invention is depicted generally at 10 in the figures. Using the present invention, an operator can alter certain AED 10 operating parameters using a personal computer (PC) connected to AED 10. The operator can retrieve, view, and change any or all of the certain operating parameters. The operator may then either store the changed operating parameters directly in the internal memory of AED 10 or on a data card, the data card being insertable into either AED 10 or PC 105.

AED 10 is capable of monitoring a patient's cardiac rhythm, detecting cardial defibrillation by comparing the monitored cardiac rhythm to nominal values, and delivering a series of therapeutic defibrillation shocks if defibrillation is detected. AED 10 is further capable of facilitating alteration of operational parameters as well.

Referring to FIGS. 1–5, an exemplary automated external defibrillator is depicted generally at 10. AED 10 includes case 12. Case 12 further defines carrying handle 14 and battery cover 16. Carrying handle 14 is formed on a front portion of case 12. Case 12 is preferably formed from a synthetic resin in the present embodiment. A battery compartment (not shown) is formed in a rear portion of AED 10. The battery compartment receives and partially encloses a battery pack 16. Battery pack 16 is removably disposed within the battery compartment. Visual maintenance indicator 20 and data access door 22 are located on the outside of case 12 to facilitate access by the operator. Data access door 22 conceals serial connector port 23 and data card slot 24.

Figure 2:
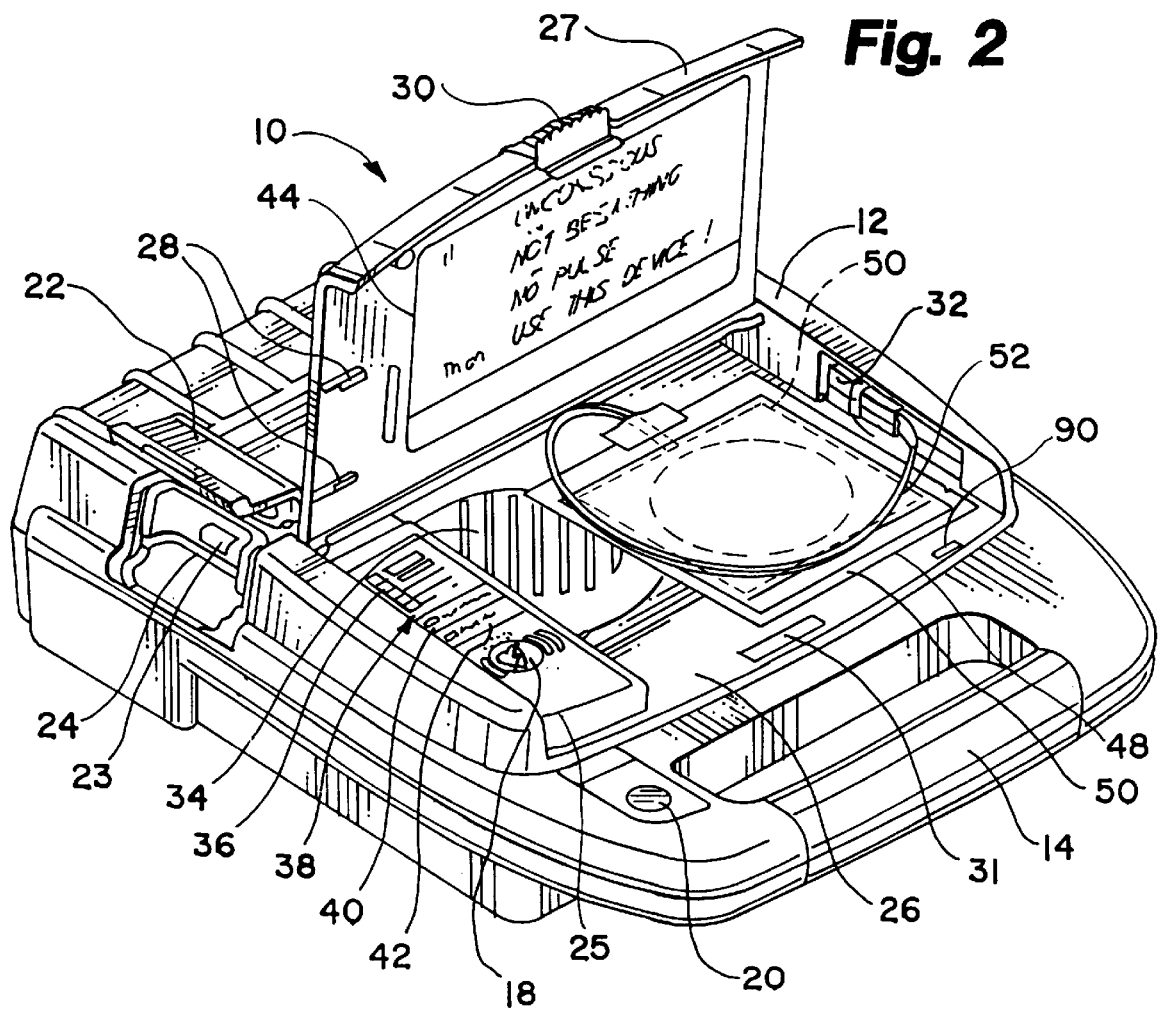
FIG. 2 is a perspective view of the AED of FIG. 1 having the lid opened.

Referring to FIG. 2, case 12 also defines panel 25 and electrode compartment 26 in a top portion thereof. Illuminatable resume/rescue switch 18 is disposed on panel 25, adjacent to electrode compartment 26. Electrode compartment 26 is enclosed by lid 27. Lid 27 is mounted to case 12 by hinges (not shown). Lid 27 covers resume/rescue switch 18 when lid 27 is in a closed disposition, as depicted in FIGS. 1 and 4. Resume/rescue switch 18 is actually a single switch with illuminatable labels. The labels alternatively indicate either a "resume" or "rescue" function. The word "rescue" appears above switch 18 and the word "resume" appears below switch 18. In operation, either "rescue" or "resume" will be illuminated, depending on whether AED 10 is prompting the operator to initiate a rescue or resume operation by activating switch 18. The inside of lid 27 may incorporate data card storage bracket 28. Data card storage bracket 28 is configured for storing a data card such as data card 29.

Data card 29 operationally inserts in data card slot 24. In this embodiment, data card 29 may store rescue information data and recorded sound received from the vicinity of AED 10 during a rescue intervention. In one embodiment, data card 29 is removable from slot 24 and the data stored thereon may be retrieved. The retrieval is then accomplished without removing AED 10 from rescue service. Data card 29 may store new altered defibrillation parameters to be downloaded to AED 10 as well. Data card 29 is commonly known as a flash card and may meet standards approved by the Personal Computer Memory Card International Association (PCMCIA).

Bayonet-type releasable latch 30 holds lid 27 closed when AED 10 is not in use by engaging receiving recess 31. Recess 31 is defined in the floor of electrode compartment 26. Lid 27 is opened by grasping the underside of latch 30, pushing in to disengage latch 30 from recess 31, and lifting upward on latch 30.

Electrode connector 32, speaker 34 and diagnostic display panel 36 are disposed on case 12 proximate electrode compartment 26. Diagnostic display panel 36 is disposed atop panel 25 adjacent illuminatable resume/rescue switch 18. Diagnostic display panel 36 includes visual "Battery Status" indicator light 38, "Electrodes" indicator light 40, and "Service" indicator light 42. Instruction and safety label 44 may be located on an inside surface of lid 27. Electrode pouch 48 may also be disposed within compartment 26. Pouch 48 may hermetically enclose and seal electrodes 50. Electrodes 50 are removably connected to electrode connector 32 by means of leads 52. In this embodiment, electrodes 50 are a pair of electrodes in a sealed package. Electrodes 50 are attached to a patient prior to a rescue intervention procedure.

Figure 5A:
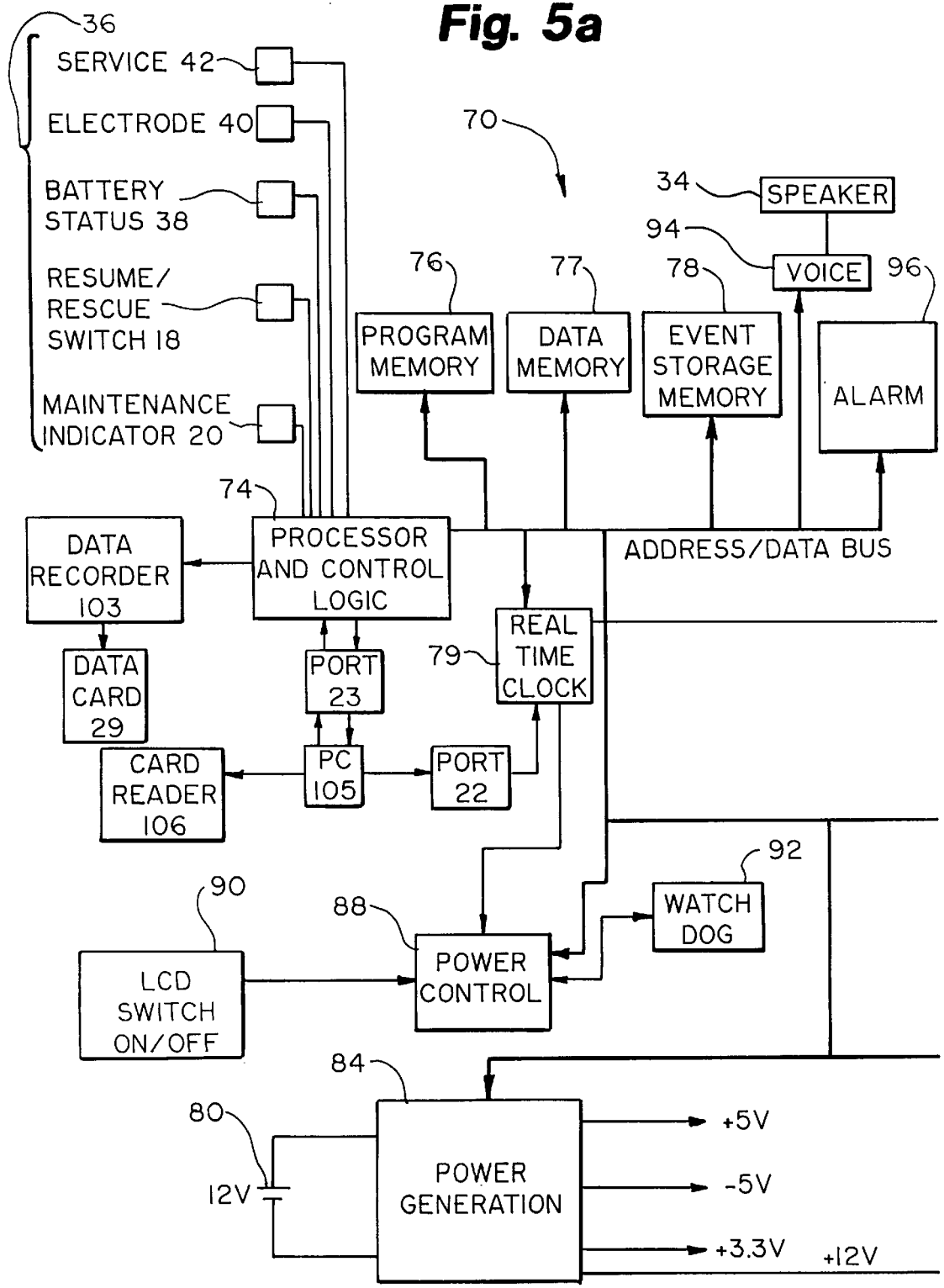
FIG. 5 is a block diagram of an electrical system of the AED.
Figure 5:
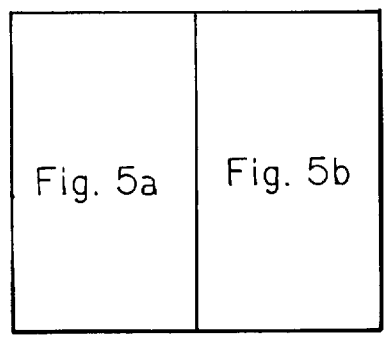
Figure 5B:
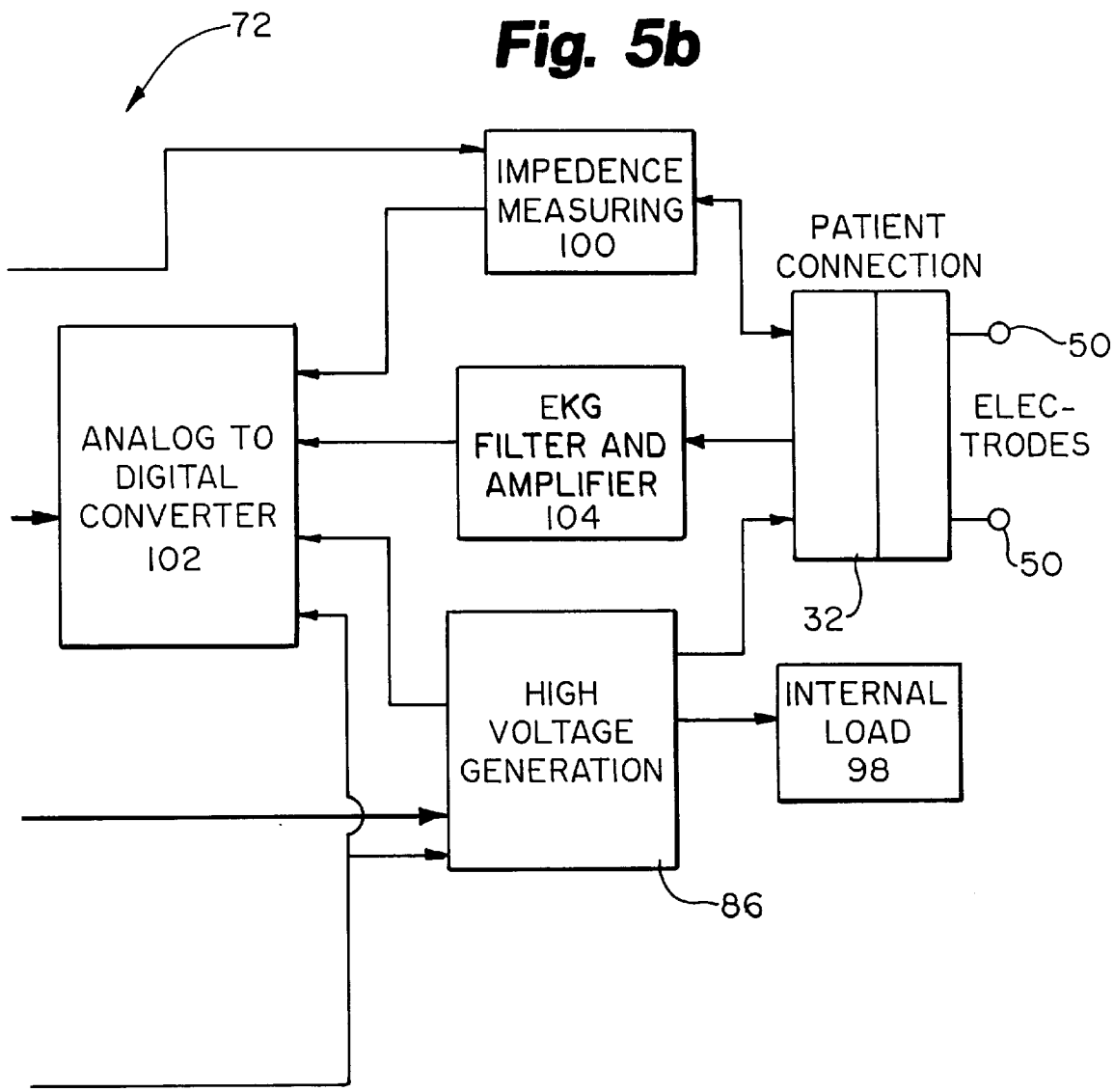

Exemplary electrical system 70 of AED 10 is depicted in the block diagram of FIG. 5. The overall operation of AED 10 is controlled by digital microprocessor-based control system 72. Control system 72, in turn, includes processor 74, program memory 76, data memory 77, event memory 78, and real time clock 79. Processor 74 is interfaced to program memory 76, data memory 77, event memory 78 and real time clock 79. The operating program executed by processor 74 is stored in program memory 76. Data memory 77 is used by processor 74 as a scratch pad memory during the execution of an operating program of AED 10.

Electrical power is provided by battery 80 disposed in battery pack 16. In a particular embodiment, battery 80 is a lithium-sulphur dioxide battery. Battery pack 16 may be removably positioned within the battery compartment of case 12. Battery 80 may include a plurality of interconnected, individual battery cells as desired. Battery 80 is connected to power generation circuit 84. "Battery Status" indicator light 38 indicates the charge status of battery 80 and prompts the operator to replace battery 80 when necessary.

During normal operation, power generation circuit 84 generates regulated ±5 V, and 12 V (actually about 5.4 V and 11.6 V) supplies with electrical power provided by battery 80. A 3.3 V supply is generally used to power real time clock 79 and lid switch 90. The 3.3 V supply also powers watch dog timer 92 when lid 27 is in a closed position (when AED 10 is in a standby mode). The ±5 V output of power generation circuit 84 functions as a back-up battery to power components of electrical system 70 during the execution of self-tests (described below). The ±5 V output of circuit 84 also activates maintenance indicators and alarms (also described below). Although not separately shown, power generation circuit 84 includes voltage level sensing circuits which are coupled to processor 74. These voltage level sensing circuits provide low battery level signals to processor 74.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment or may be a Hall effect sensor. Lid switch 90 provides signals to processor 74 indicating whether lid 27 is open or closed. Serial connector port 23 is coupled to processor 74 for two-way serial data transfer using an RS-232 protocol.

Resume/rescue switch 18 (and the "rescue" and "resume" indications discussed above), "Maintenance" indicator 20, "Battery Status" indicator light 38, "Electrodes" indicator light 40, and "Service" indicator light 42 of diagnostic display panel 36, voice circuit 94 and piezoelectric audible alarm 96 are also connected to processor 74. Voice circuit 94 is connected to speaker 34. In response to voice prompt control signals from processor 74, voice circuit 94 and speaker 34 generate audible voice prompts provided to the operator.

High voltage generation circuit 86 is also connected to and controlled by processor 74. High voltage generation circuits such as circuit 86 are known and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode. During the charge mode of operation, one set of semiconductor switches (not separately shown) causes a plurality of capacitors (not separately shown) to be charged in parallel to a potential of about 400 V. Each capacitor is charged by power supplied by power generation circuit 84. Once charged, and in response to discharge control signals from processor 74, high voltage generation circuit 86 is operated in a discharge mode. During discharge, the capacitors are discharged in series by another set of semiconductor switches (not separately shown) to produce high voltage defibrillation pulses. The defibrillation pulses are applied to the patient by electrodes 50, via electrode connector 32. Electrode connector 32 is connected to high voltage generation circuit 86. Under certain circumstances (described below), processor 74 causes high voltage generation circuit 86 to be discharged through internal resistive load 98 rather than connector 32.

Impedance measuring circuit 100 is connected to electrode connector 32 and real time clock 79. Impedance measuring circuit 100 is also interfaced to processor 74 through analog-to-digital (A/D) converter 102. Impedance measuring circuit 100 receives a clock signal with a predetermined magnitude from clock 79 and applies the signal to electrodes 50 through connector 32. The magnitude of the clock signal received back from electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., a measure of the attenuation of the applied signal). For example, if the conductive adhesive on electrodes 50 is too dry, if electrodes 50 are not properly connected to connector 32, or if electrodes 50 are not properly positioned on the patient, a relatively high resistance (e.g., greater than about 200 ohms) will be present across connector 32. The resistance across connector 32 will be between about 25 and 175 ohms when fresh electrodes 50 are properly positioned on the patient with good electrical contacts. The signal representative of the impedance measured by circuit 100 is digitized by A/D converter 102, then relayed to processor 74.

AED 10 also includes data recorder 103 and electrocardiogram (ECG) filter and amplifier 104. Data recorder 103 is interfaced to processor 74. Data recorder 103 is positioned internally within AED 10 adjacent to data card slot 24, so as to be ready to accept data (rescue information) card 29. ECG filter and amplifier 104 is connected between electrode connector 32 and A/D converter 102. The ECG or cardiac rhythm of the patient is sensed by electrodes 50 on the patient and processed by ECG filter and amplifier 104 in a conventional manner, then digitized by A/D converter 102 before being relayed to processor 74.

The rescue mode of operation of AED 10 is initiated when an operator opens lid 27 to access electrodes 50. An opened lid 27 is detected by lid switch 90. Lid switch 90 functions as an on/off switch for AED 10. In response to lid switch 90 being activated when lid 21 is opened, power control circuit 88 activates power generation circuit 84 and initiates the rescue mode operation of processor 74. Processor 74 then begins its rescue mode operation by: 1) switching maintenance indicator 20 to a maintenance required state (a red visual display in one embodiment); 2) flashing the "rescue" light associated with resume/rescue switch 18 and the indicator lights on diagnostic display panel 36; and 3) performing a lid opened self-test.

During the lid opened self-test, checks performed by processor 74 include: 1) the charge state of battery 80; 2) the interconnection and operability of electrodes 50 (if the electrode test is enabled); 3) the state of event memory 78; 4) the functionality of real time clock 79; and 5) the functionality of A/D converter 102. The charge state of battery 80 is checked by monitoring the voltage level signals provided by power generation circuit 84 and comparing these voltage level signals to predetermined nominal values. If battery 80 is determined to have a low charge, the "battery status" indicator 38 on diagnostic display panel 36 will indicate the sensed status. If the electrode self-test is conducted, the interconnection and operability of electrodes 50 are checked by monitoring the impedance signals provided by impedance measuring circuit 100. If electrodes 50 are missing or unplugged from connector 32, if electrodes 50 are damaged, or if the conductive adhesive on electrodes 50 is too dry, processor 74 will illuminate "Electrodes" indicator light 40 on diagnostic display panel 36.

Also, during the lid opened self-test, processor 74 accesses event memory 78 to determine whether data from a previous rescue operation are still stored therein. If data from a previous rescue are still present, processor 74 causes the "resume" indicator associated with resume/rescue switch 18 on diagnostic panel 36 to be illuminated and initiates the generation of a "Clear Memory" voice prompt. If resume/rescue switch 18 is pressed by the operator following the activation of these indicators, processor 74 clears event memory 78 and proceeds with its rescue mode of operation. The functionality of real time clock 79 and A/D converter 102 are checked by monitoring the outputs of these circuit elements for expected signals. Diagnostic display panel "Service" light 42 is illuminated by processor 74 if faults are identified in real time clock 79 or in A/D converter 102.

If the lid opened self-test is successfully completed, processor 74 switches maintenance indicator 20 to an operational state and initiates the rescue mode of operation of AED 10. In the rescue mode of operation voice circuit 94 generates audible voice prompts through speaker 34 to guide the operator through the operations of AED 10 and, if necessary, delivery of a defibrillation pulse to the patient. AED 10 determines its rescue mode steps of operation by monitoring the impedance across electrode connector 32 and the patient's cardiac rhythm.

Closing lid 27 after rescue mode operation activates processor 74 to initiate and perform a lid closed self-test. During the lid closed self-test, processor 74 performs a comprehensive check of the status and functionality of AED 10 including: 1) the state of event memory 78; 2) the functionality of real time clock 79; 3) the functionality of A/D converter 102; 4) the functionality of program memory 76, data memory 77, and event memory 78; 5) the charge state of battery 80; and 6) the interconnection and operability of electrodes 50 (if enabled to do so). The state of event memory 78, the state of battery 80, the interconnection and operability of electrodes 50, and the functionality of real time clock 79 and A/D converter 102 are checked in a manner identical to that described above with reference to the lid opened self-test.

Conventional memory test routines are also implemented to check the functionality of program memory 76, data memory 77 and event memory 78. Maintenance indicator 20 is switched to its maintenance required state by processor 74 if faults are identified during the lid closed self-test. No audible alarms are actuated if faults are identified in the charge state of battery 80 or the interconnection or functionality of electrodes 50 during the lid closed self-test.

A daily self-test is also initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 leaves maintenance indicator 20 in a maintenance required state if faults are identified during the daily self-test.

Processor 74 also initiates and performs a weekly self-test at a predetermined time one day each week. During the weekly self-test, processor 74 performs all the component check operations described above that are performed during the daily self-test. In addition, processor 74 causes high voltage generation circuit 86 to sequentially operate in its charge and discharge modes, the charge being directed to internal resistive load 98. When high voltage generation circuit 86 is operating in a charge mode, processor 74 monitors the time required to charge the circuit's capacitors and the capacitor voltage. A fault is identified if either time is outside nominal conditions. Maintenance indicator 20 and alarm 96 are actuated in the manner described above if any faults are identified during the weekly self-test. All performed test and patient data may be recorded in event memory 78.

Watch dog timer 92 is set to time watch dog time-out periods of about thirty hours (i.e., a period greater than the twenty-four hour periods between daily self-tests). Watch dog timer 92 is reset by processor 74 at the beginning of each daily self-test and each time lid 27 is opened. In the event control system 70 malfunctions and watch dog timer 92 times out, internal hardware switches maintenance indicator 20 to the maintenance required state and actuates alarm 96 to alert the operator to the fact that AED 10 requires maintenance.

AED 10 facilitates archival storage of rescue information. Data representative of the operation of AED 10 and patient data may be stored in event memory 78 during rescue mode operation. However, if data card 29 is inserted into card slot 24 before the beginning of a rescue attempt, the rescue information is automatically recorded by data recorder 103 onto data card 29, thereby also facilitating archival storage of rescue information. Stored data representative of the operation of AED 10 may include the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 86, and 5) the actuation of the resume/rescue switch 18 in the rescue mode. The actual time base of the patient's cardiac rhythm (ECG information) may also be stored. Data representative of the patient may include the monitored cardiac rhythm, key events detected during the rescue operation, and sound occurring within the vicinity of AED 10.

Following a rescue, the stored data may be retrieved from event memory 78 through the use of computer (PC) 105 interfaced to serial connector port 23. The details of this interface are discussed below. Real time clock 79 can also be set through the use of PC 105 interfaced to port 22. If the rescue data were stored on data card 29 and data card 29 remains in slot 24, the data may also be retrieved through the use of PC 105 interfaced to serial connector port 23. Alternatively, data card 29 may be removed from slot 24 and inserted into an appropriate card reader 106, directly connected to PC 105, such as a PCMCIA type I card reader.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the twenty most recently performed tests are stored in memory 78. The stored self-test records may be retrieved from memory 78 through PC 105 interfaced to serial connector port 23. Each self-test is powered by the battery pack. The battery pack may also be coupled to real time clock 79 to continuously provide power thereto.

Selected operating parameters determine how AED 10 administers defibrillation shocks (or pulses), performs self-tests, and stores rescue data. These selected parameters may be modified by an exemplary software-enabled protocol as described below. As indicated in Table 1, these parameters may include "Second Shock Energy", "Maximum Shocks Per Rescue", "Same Energy After Conversion", "Daylight Savings", "Electrode Test", and "External Memory Storage".

TABLE 1

| Function | Default | Selectable Options |
| --- | --- | --- |
| Second Shock Energy (J) | 300J | 200J |
| Maximum Shocks Per Rescue | 255 | 6 to 255 |
| Same Energy After Conversion | Enabled | Disabled |
| Daylight Savings | Enabled | Disabled |
| Electrode Test | Enabled | Disabled |
| External Memory Storage | Long Rescue | Voice Record |

In a rescue intervention, a series of shocks may be delivered to a patient. The present invention provides for varying the energy of the second shock. The Second Shock Energy parameter determines the energy in Joules (J) delivered in the second defibrillation pulse to a patient by AED 10. The default value for the Second Shock Energy parameter is 300 J; however, a value of 200 J may be selected.

The Maximum Shocks Per Rescue parameter determines the number of defibrillation pulses delivered by AED 10 during a rescue. The default value for the Maximum Shocks Per Rescue parameter is 255; but, any number of defibrillation pulses between 6 and 255 inclusive may be selected.

The Same Energy After Conversion parameter determines whether the same energy as the previous defibrillation pulse will be delivered when the patient assumes (or converts to) a normal sinus heart rhythm, but then reverts back to a shockable cardiac rhythm. The default status for the Same Energy After Conversion parameter is enabled, e.g., the same energy as the previous pulse will be delivered. This parameter may be disabled by the present protocol as described below.

The Daylight Savings Time parameter automatically adjusts real time clock 79 to adjust to daylight savings time when enabled; however, this parameter may be disabled as described below.

The Electrode Test parameter provides for the electrode self-test to occur during self-tests as described above. The default setting for the Electrode Test parameter is to perform the electrode tests; however, this parameter may be disabled. This would be desirable if certain electrodes not compatible with the self-test were used with AED 10.

The External Memory Storage parameter determines whether up to five hours of electrocardiogram (ECG) and event data or whether up to 20 minutes of ECG and event data, plus ambient sound, will be recorded during a rescue in an external memory storage device such as card 29 or in memory 78. The default setting for the External Memory Storage parameter is "Long Rescue" in which up to five hours of ECG and event data, but not ambient sound, are recorded. However, a "Voice Record" setting will enable ECG data, event data, and ambient sound to be recorded for up to 20 minutes.

Selected parameter settings may be stored in program memory 76 or data (options) card 29. Data card 29 may be inserted into slot 24 of AED 10. Card 29, when first inserted into adaptor 108, may also be inserted into card reader 106. PC 105 must have a compatible operating system in order to be employed in the present application. Once the selected parameters have been stored on data card 29, they may then be transferred to several AED 10 units by the operator.

The implementing program of the present invention may be installed from a diskette drive of PC 105. During installation, a serial communications port is manually or automatically selected and a program group box (such as SurVivaLink®) is generated. A program icon (such as MDLink™) will also be generated and may appear within the program group box.

Figure 7:
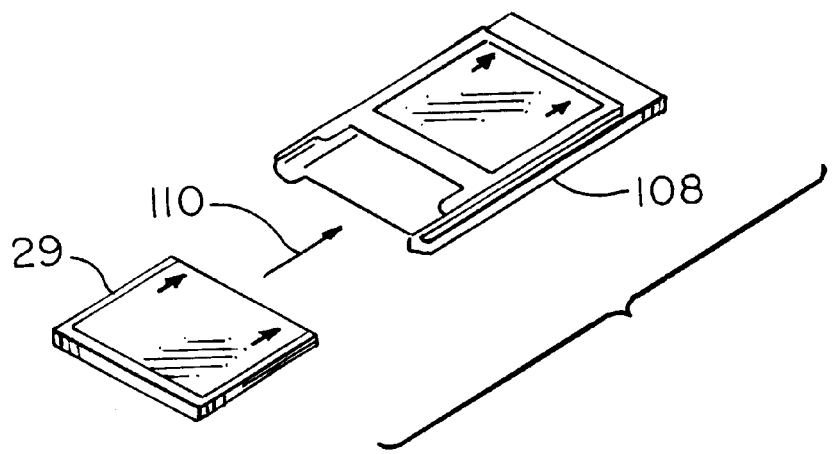
FIG. 7 depicts an options card being inserted into an adaptor prior to being inserted into a PC.

Before initiating the program to determine and/or alter the above-described parameter values, the operator first determines where the selected parameter values will be stored. The parameter values may be stored in program memory 76 of AED 10 or data card 29. A given data card 29, containing the stored parameter values, may be inserted in slot 24 of AED 10 or into card reader 106 of PC 105 (after being inserted into adaptor 108), as depicted in FIG. 7.

Before the Set, Get, and Options commands (described below) may be used, AED 10 must be electrically connected to the PC via serial communications cable 112 as depicted in FIG. 4. Cable 112 includes connectors 114, 116. Connector 114 (e.g., a RJ11 modular plug) on serial communications cable 112 is inserted into port 23 of AED 10. Connector 116 is coupled to PC serial port 118. In this embodiment, connector 116 is a 9-pin, male D-sub connector. Lid 27 of AED 10 must be in an open position for parameter value transfer to occur.

In a preferred embodiment, the implementing exemplary program of the present invention has been written in $C^{++}$ and has been compiled for use. However, the person of ordinary skill in the art will readily appreciate that any of a number of programming languages may be used.

Figure 8:
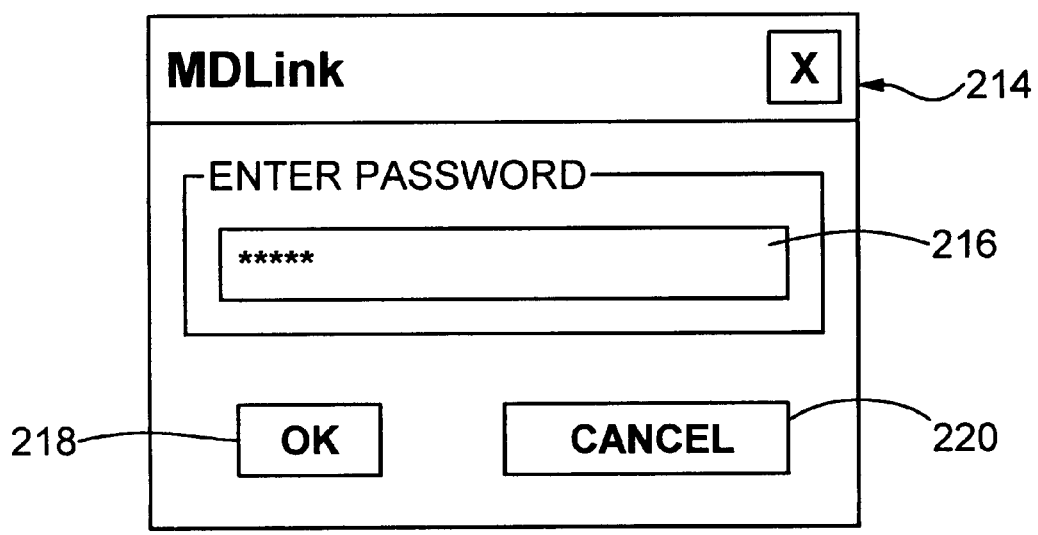
FIG. 8 depicts the Password Entry Screen Display generated by the program of the present invention.

Referring to FIG. 6A, the program is initiated in step 210 on PC 105, in which the program has been installed. Program initiation is accomplished by double-clicking the program icon with a mouse. The program may also be initiated by double-clicking the program file via a file manager in certain operating systems. After the program is initiated, a password dialogue occurs in step 212. Referring to FIG. 8, password dialogue screen 214 displayed on the monitor of PC 105 includes "Enter Password" window 216, "OK" button 218, and "Cancel" button 220. In step 222, the operator keys in a password character string. An "X" or other indicium may appear in window 216 for each character entered. After keying in the password, the operator clicks OK button 218 or holds down the Alt key and depresses the "O" key. Referring again to FIG. 6A, in step 224, the program compares the password entered by the operator in step 222 to a previously entered password. If a match does not occur, an invalid password dialogue (not shown) is momentarily displayed in step 226, password dialogue screen 214 is again displayed, and the operator again enters a password in step 222. If the input password entered by the operator in step 222 is correct, step 228 displays Main Screen 230. The operator may also select Cancel button 220. If this selection is made, the program in not initiated.

Figure 9:
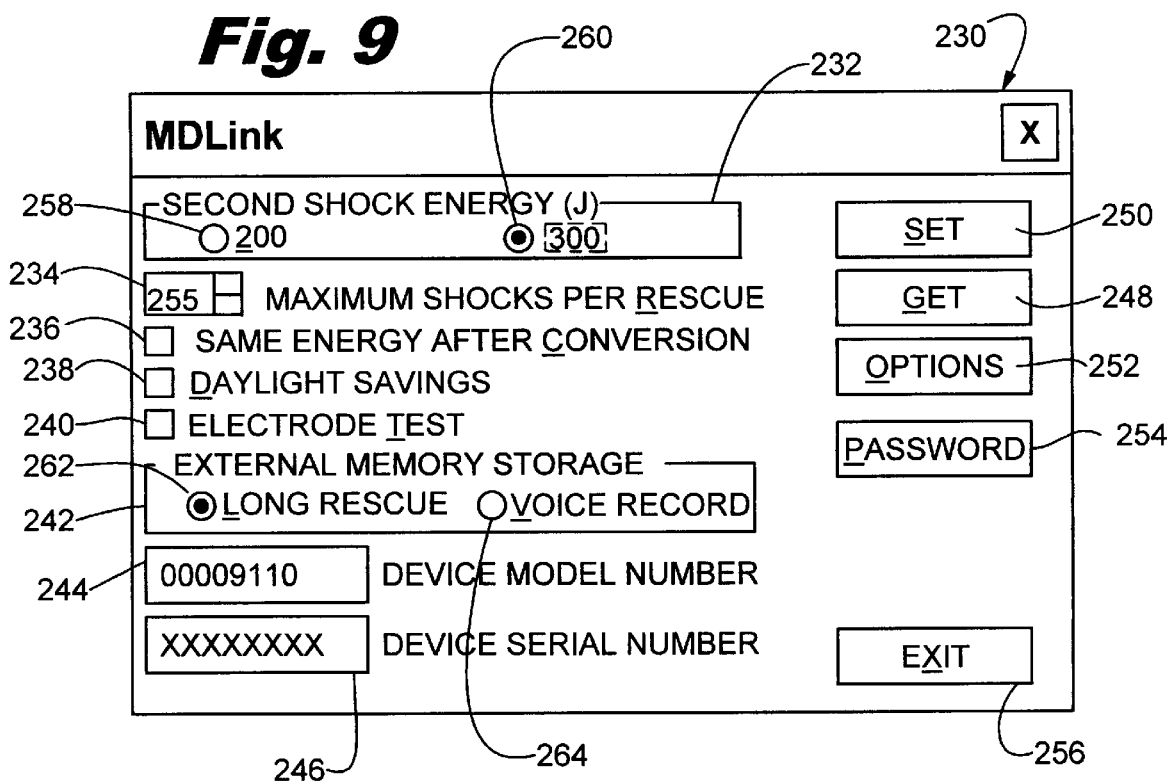
FIG. 9 depicts the Main Screen Display generated by the program of the present invention.

As depicted in FIG. 9, exemplary Main Screen 230 displays on the monitor of PC 105 certain default parameter settings when step 228 is executed. Main Screen 230 includes Second Shock Energy window 232, Maximum Shocks Per Rescue window 234, Same Energy After Conversion window 236, Daylight Savings window 238, Electrode Test window 240, External Memory Storage window 242, Device Model Number window 244, Device Serial Number window 246, Get button 248, Set button 250, Options button 252, Password button 254, and Exit button 256. Second Shock Energy window 232 further includes "200" selection 258 and "300" selection 260. External Memory Storage window 242 further includes Long Rescue selection 262 and Voice Record selection 264.

As discussed above, Main Screen 230 appears in step 228 (FIG. 6A) with default parameter settings indicated in windows 232–242. These respective default settings indicate a Second Shock Energy of 300 J, Maximum Shocks Per Rescue of 255, Same Energy After Conversion enabled, Daylight Savings enabled, Electrode Test enabled, and External Memory Storage Configured for Long Rescue. Respective selectable options are a Second Shock Energy of 200 J, between 6 and 254 Maximum Shocks Per Rescue as desired, Same Energy After Conversion disabled, Daylight Savings disabled, Electrode Test disabled, and External Memory Storage Configured for Voice Record.

Each of selections 248–254 may be actuated by using a mouse selector of PC 105. Alternatively, buttons 248–256 may be selected by holding down the Alt key of the keyboard of PC 105 and depressing the key corresponding to the underlined letter of the button name.

Figure 6B:
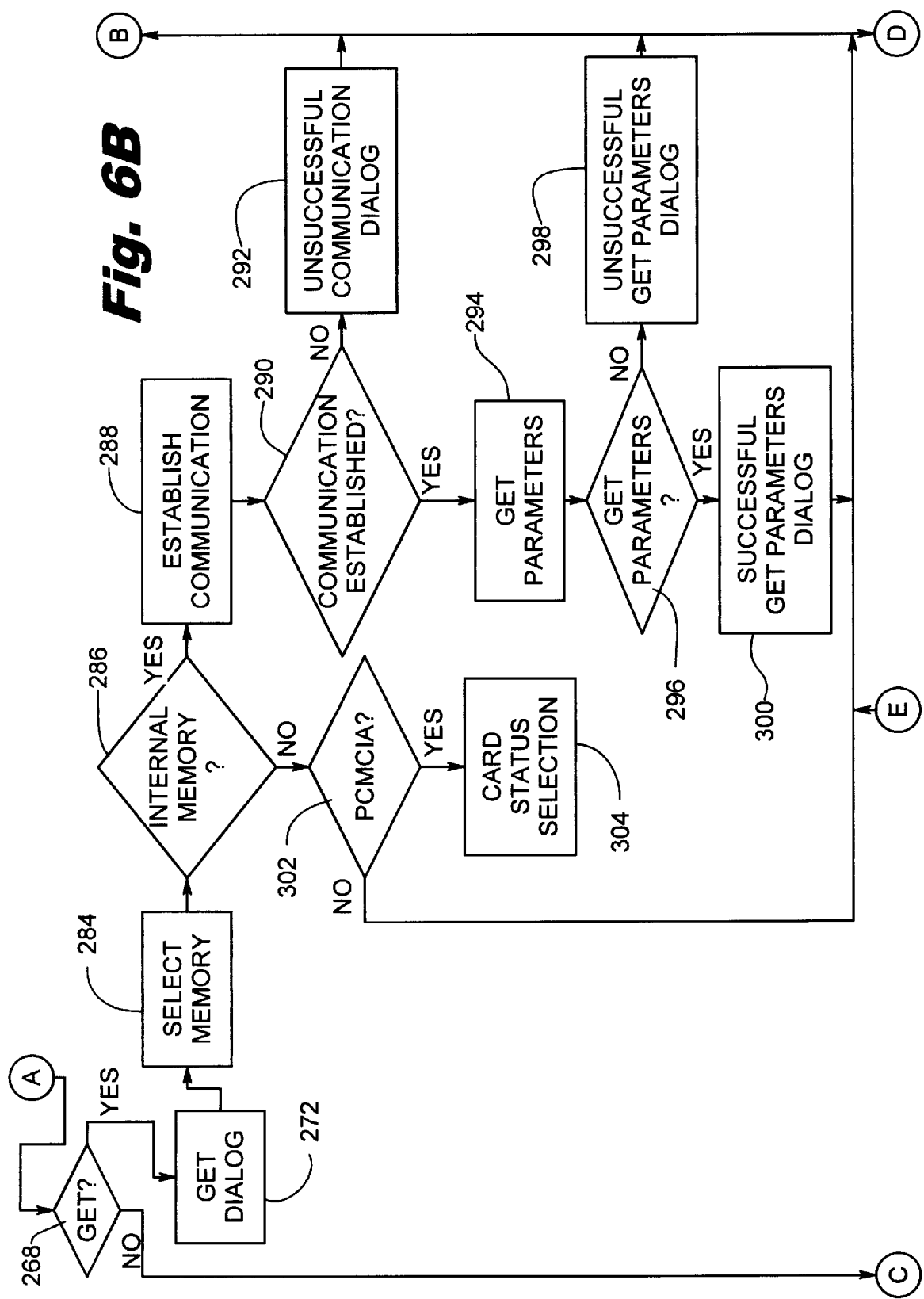
Figure 10:
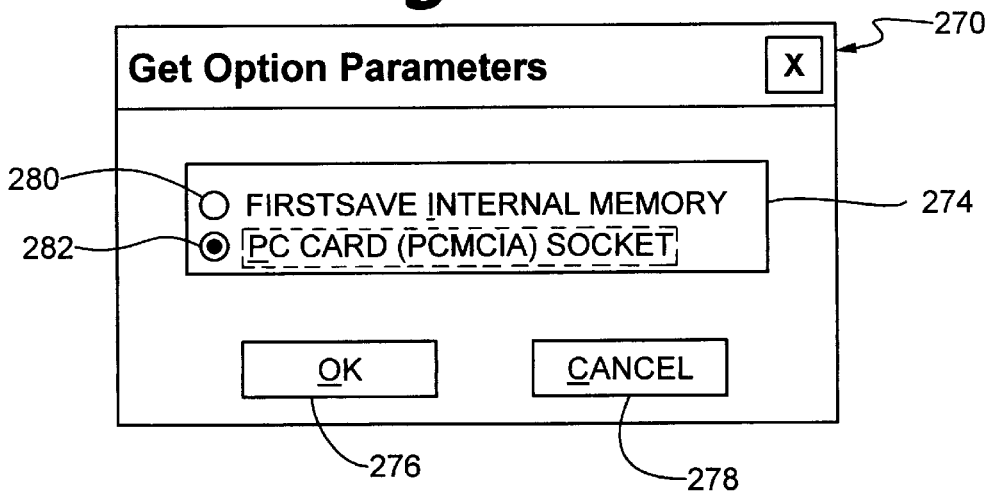
FIG. 10 depicts the Get Option Screen Display generated by the program of the present invention.

In step 266 of FIG. 6A, the operator selects one or more defibrillation parameters to be altered and/or actuates one of selections 248–256. In step 268 of FIG. 6B, the program determines whether Get selection 248 has been selected. If so, Get Option Parameters screen 270 (FIG. 10) is displayed on the monitor of PC 105 in step 272. Actuating Get selection 248 retrieves parameters from internal (program) memory 76 or from data card 29. Get Option Parameters screen 270 includes window 274, OK button 276, and Cancel button 278. Window 274 further includes FirstSave Internal Memory selection 280 and PC Card (PCMCIA) Socket selection 282. Selecting Internal Memory 280 permits the operator to retrieve parameters from Internal Memory 76. Selecting PC card (PCMCIA) socket permits the operator to retrieve parameters from data card 29. The operator selects one of selections 280, 282 in step 284 of FIG. 6B. Step 286 then determines whether selection 280 was selected. If selection 280 was selected, communications are established to program memory 76 in step 288. If Cancel button 278, or any Cancel button, is actuated during the execution of program 200, the present protocol routes to Main Screen 230.

In step 290 of FIG. 6B, the program determines whether the communication to program memory 76, attempted in step 288, has in fact been established. If communication has not been established in step 288, unsuccessful communications dialogue (not depicted) is displayed to the operator in step 292 and the program returns to Main Screen 230. If communication was established in step 288, the program executes Get Parameters step 294.

In step 294, the defibrillation parameter settings are retrieved from program memory 76 and are displayed to the operator on main screen 230 (FIG. 9). Step 296 determines whether Get Parameters step 294 was successful in retrieving the parameter settings. If not, Unsuccessful Get Parameters dialogue (not depicted) is displayed to the operator in step 298 and the program then returns to Main Screen 230. If step 294 was successful, Successful Get Parameters dialogue (not depicted) is displayed to the operator in step 300. The program then routes to Main Screen 230.

Step 302 determines whether selection 282 (see FIG. 10) was made by the operator in step 284. If so, Card Status Selection step 304 is executed and steps 294–300are then executed as described above. If neither selection 280 nor selection 282 was selected, (i.e. Cancel button 278 was actuated), the program directs to Main Screen 230.

Set selection 250 on Main Screen 230 may be actuated by the operator. Actuating Set selection 250 stores selected parameters in designated storage devices (described below). Step 306 (FIG. 6C) determines whether Set selection 250 was actuated by the operator. If Set selection 250 was actuated, the parameter selected by the operator in Maximum Shocks Per Rescue window 234 is analyzed in step 308. If the value for window 234 is less then 6 or greater than 255, Invalid Maximum Shock dialogue (not shown) is displayed in step 310 and the value for the Maximum Shocks Per Rescue parameter in window 234 is then set to the default parameter, 255, in step 312. Set Options dialog (not depicted) is then displayed to the operator in step 314. In step 316, the program determines whether parameter values selected in windows 232–242 of Main Screen 230 (FIG. 9) are accepted.

Figure 15:
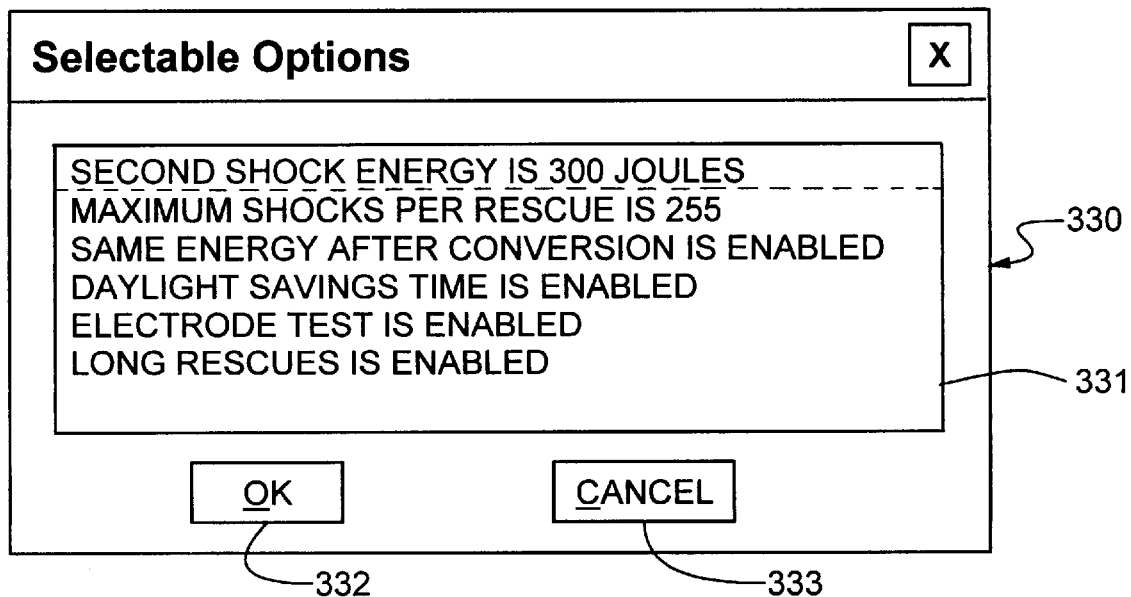
FIG. 15 depicts the Selectable Options Screen Display generated by the program of the present invention.

If the parameter values selected in windows 232–242 are accepted, a storage device is selected in step 318, wherein Set Option Parameters screen 319 is displayed to the operator to prompt a storage device selection. Referring to FIG. 16, Set Option Parameters screen 319 includes window 320, OK selection 321, and Cancel selection 322. Window 320 includes FirstSave Internal Memory selection 323, FirstSave Card Slot selection 324, and PC Card (PCMCIA) Socket selection 325. If the operator selects selection 323, the parameters will be stored in program memory 76. If the operator selects selection 324, the parameters will be stored on card 29 inserted in slot 24. If the operator selects selection 325, the parameters will be stored on card 29 inserted in card reader 106 of PC 105. The operator then selects one of selections 323–325 and activates OK selection 321. If the storage device selected in step 318 was Internal Memory selection 323, step 326 routes logic to establish communications to program memory 76 in step 327. When communications have been established, step 328 displays Selectable Options screen 330, depicted in FIG. 15.

Selectable Options screen 330 includes window 331, OK selection 332, and Cancel selection 333. Window 331 depicts parameter values to be stored in program memory 76. The operator views these parameter values and actuates OK selection 332 if the parameter values are as desired. In step 334, the selected parameters are stored in internal memory and Successful Set Parameters dialogue (not shown) is displayed in step 336. The program then directs to Main Screen 230.

Figures 1, 6C:
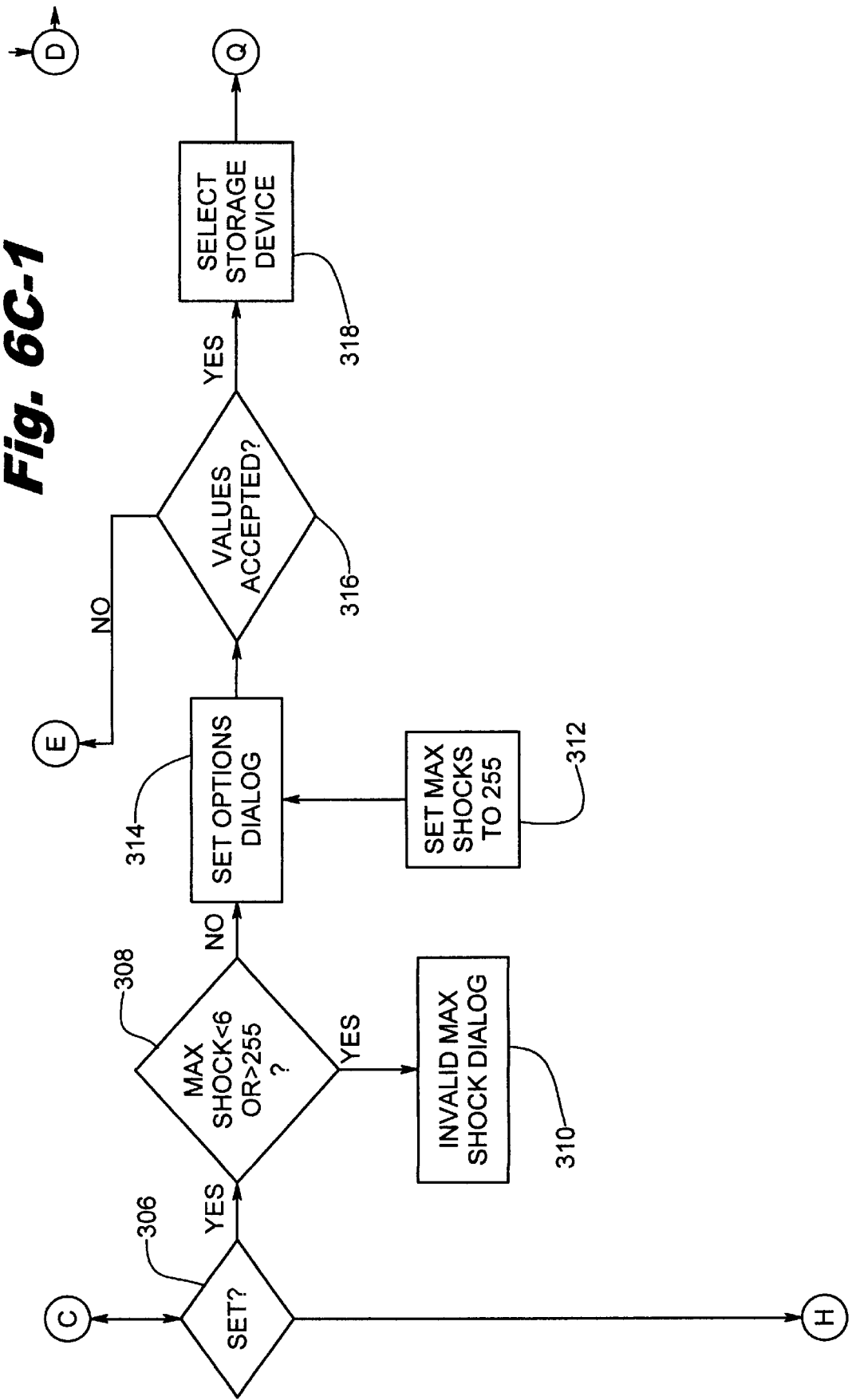
Figures 2, 6C:
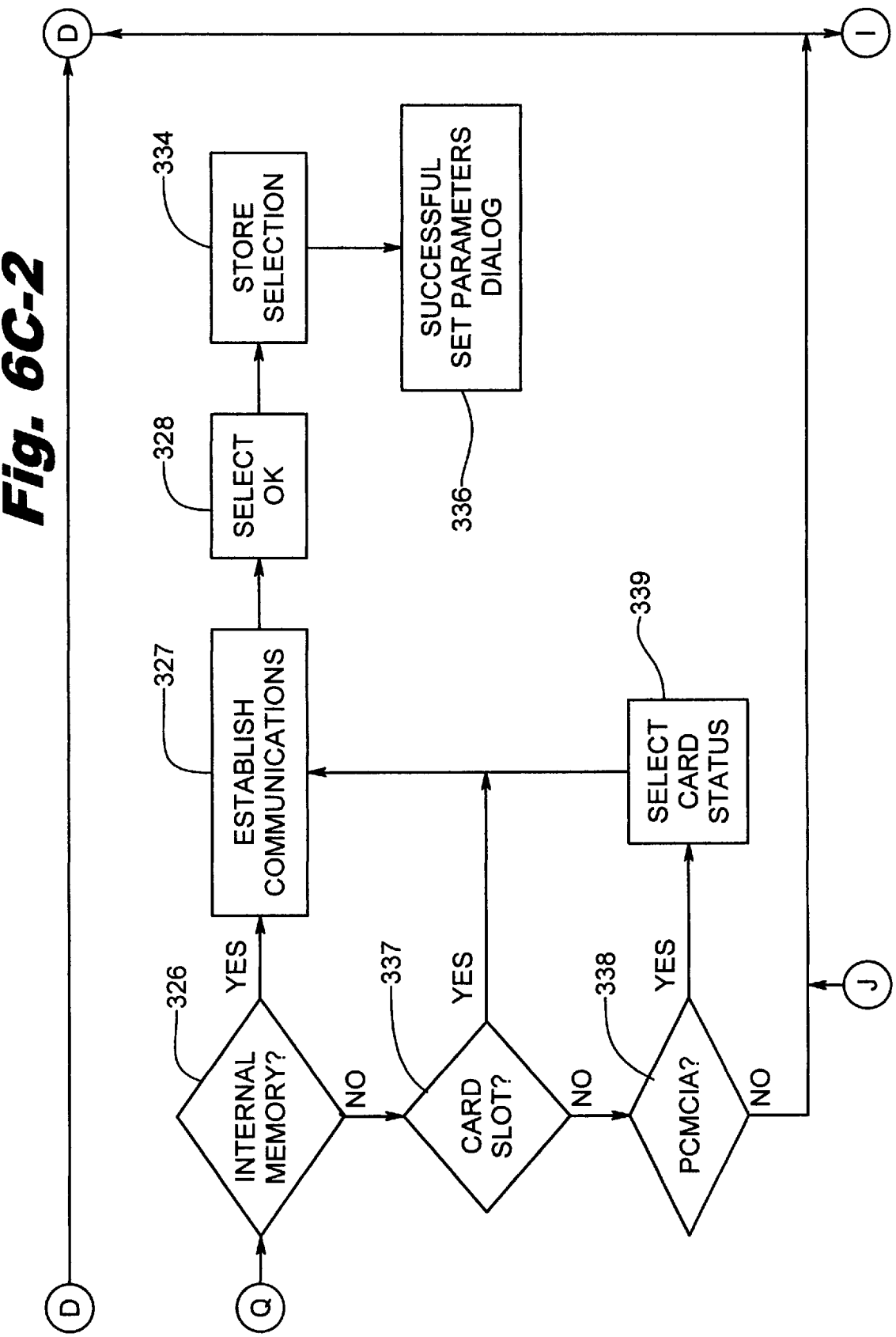

Referring to FIG. 6C, if Internal Memory was not selected in step 318, step 326 directs logic flow to step 337. In step 337 it is determined whether Card Slot selection 324 (card slot 24 of AED 10) was selected. If so, logic flow is directed to steps 327–336 as described above. However, communication is established to card slot 24 and selected parameters are stored on card 29 in card slot 24 in step 334.

Figure 12:
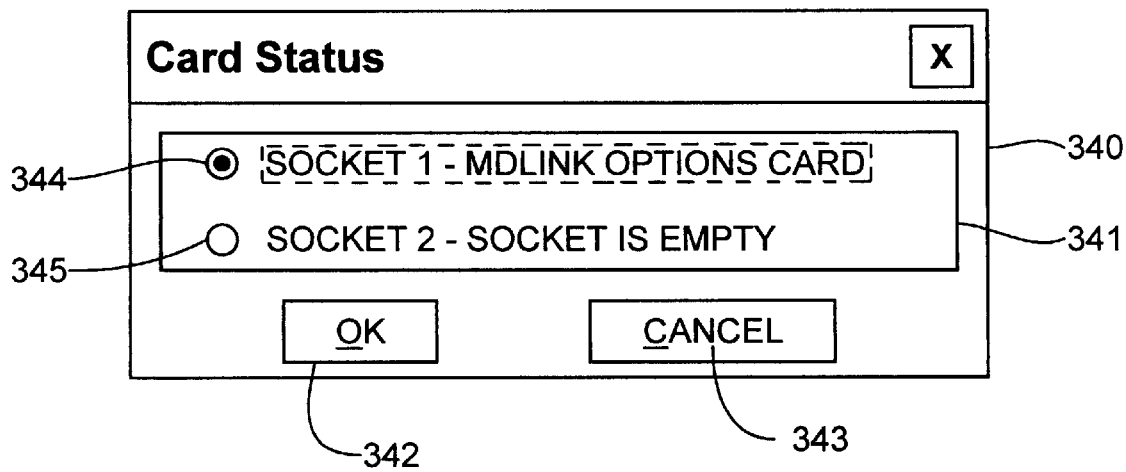
FIG. 12 depicts the Card Status Screen Display generated by the program of the present invention.

If the storage device selected in step 318 is neither internal memory nor card slot 24, step 337 directs logic flow to step 338. Step 338 determines whether PC Card (PCMCIA) Socket selection 325 was selected. If selection 325 was selected, step 339 displays Card Status screen 340. Card Status screen 340 is depicted in FIG. 12 and includes window 341, OK selection 342, and Cancel selection 343. Card status screen 340 permits the operator to erase the parameters stored on card 29. Window 341 includes respective Socket 1 and Socket 2 selections 344, 345. The operator selects the socket 344 or 345, as desired, and actuates OK selection 342. Selection of socket 344 followed by selection of OK selection 342 erases the data on card 29. Logic flow then directs to steps 327–336 and proceeds as described above with reference to FIG. 6C. However, communications are established to the designated socket (e.g., card reader 106 of PC 105) in step 327 and parameter selections are stored on the PCMCIA Card in the designated socket in step 334. If neither internal memory 76, card slot 24, nor PCMCIA 338 was selected, logic flow directs to Main Screen 230 without the values selected in windows 232–242 of Main Screen 230 having been stored.

Figures 1, 6D:
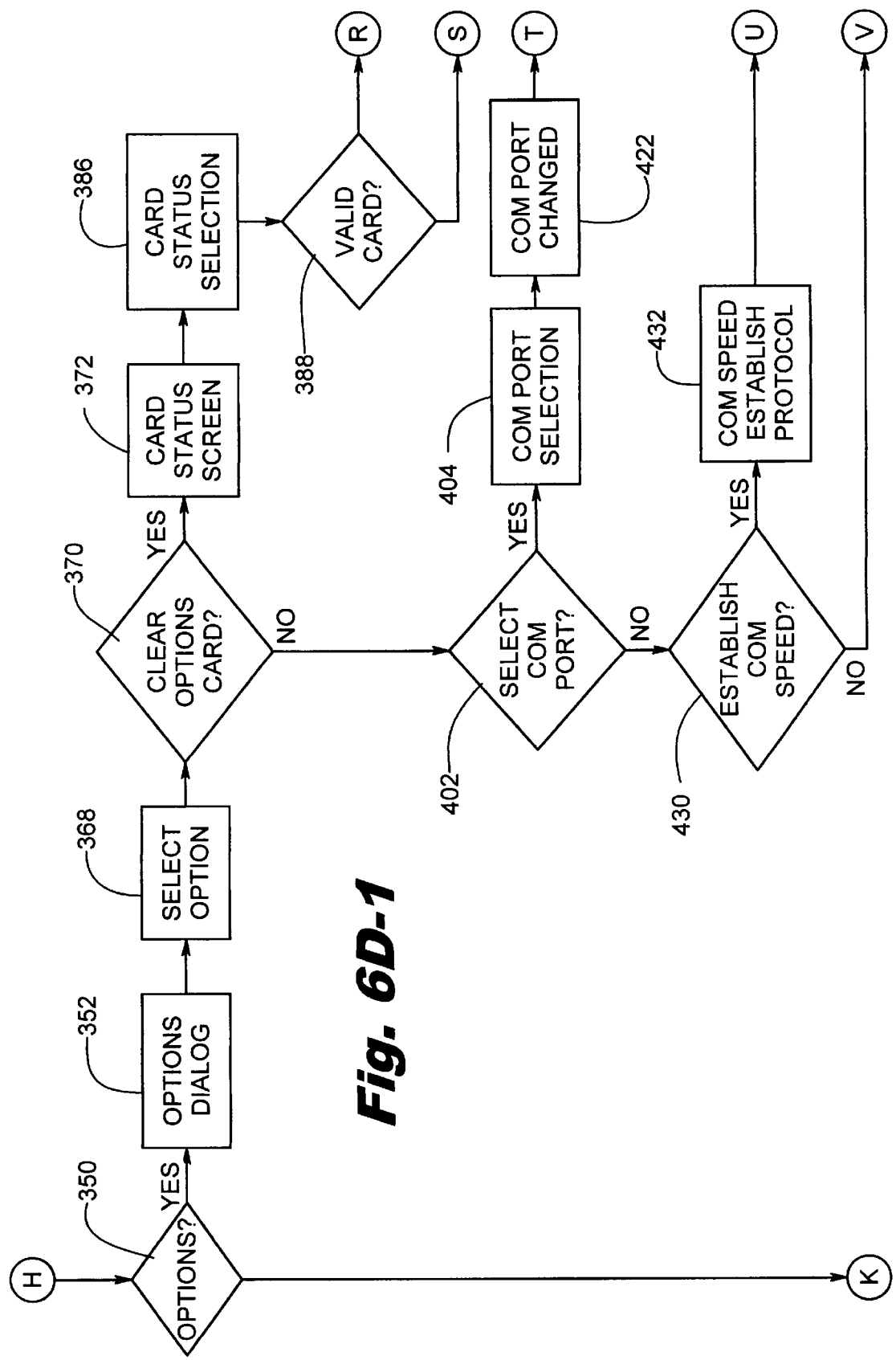
Figures 2, 6D:
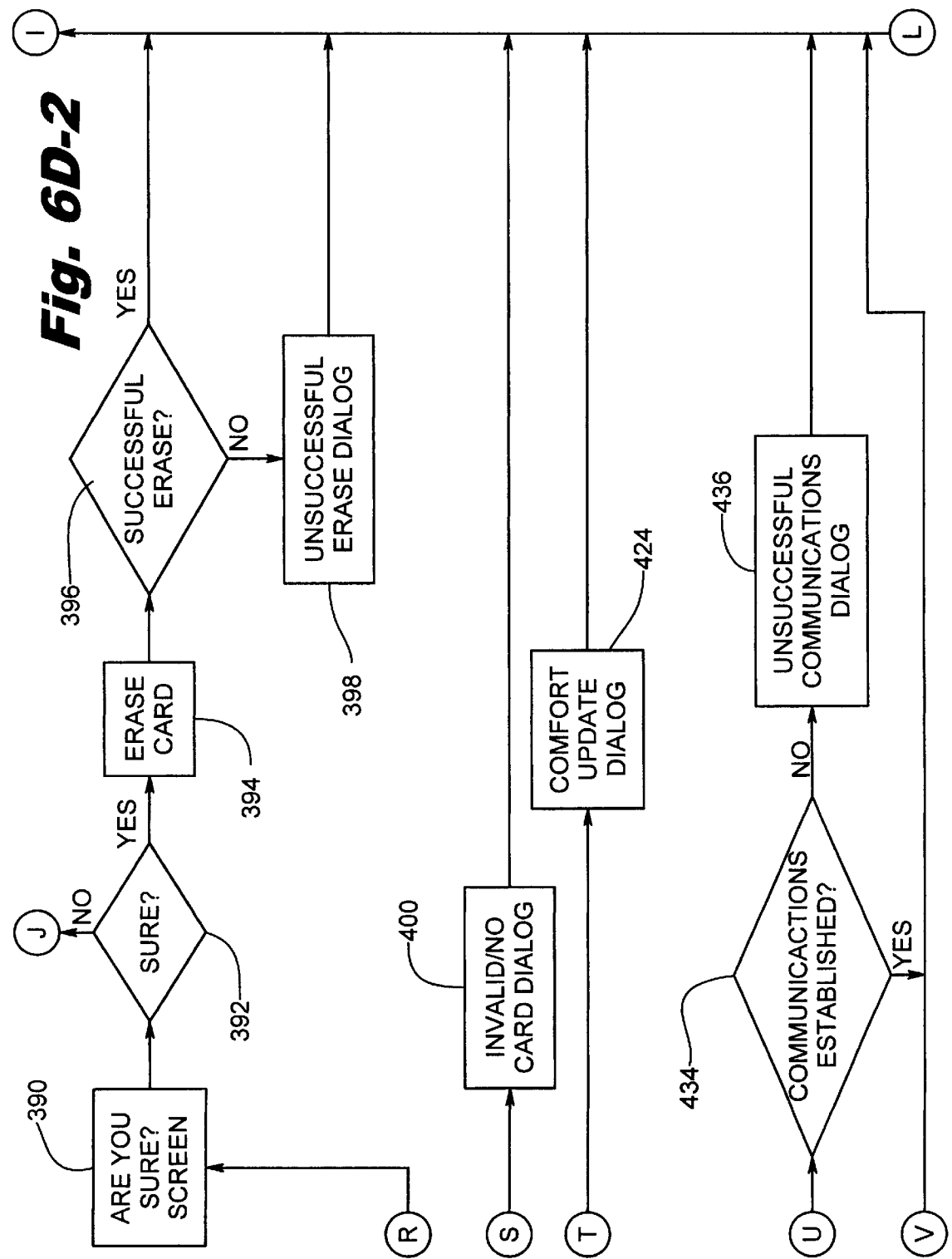
Figure 11:
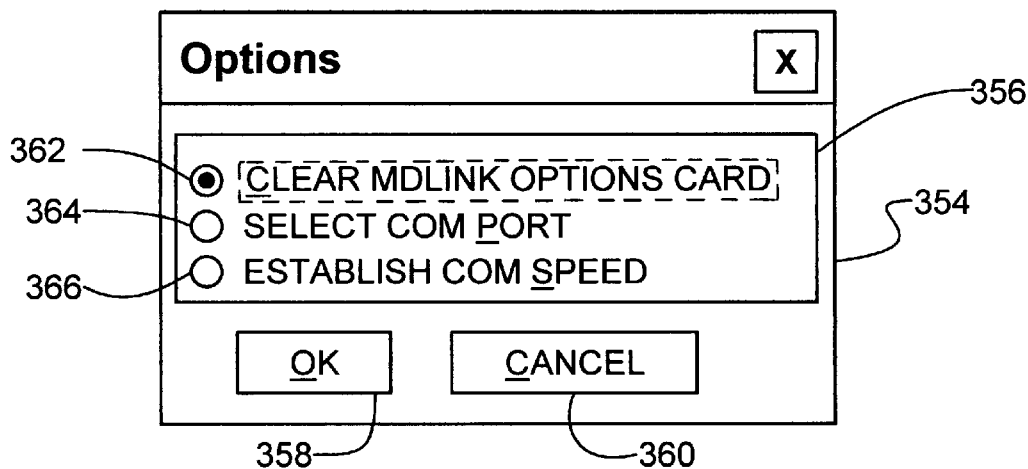
FIG. 11 depicts the Options Screen Display generated by the program of the present invention.

If Options selection 252 in FIG. 9 was selected, step 350 (FIG. 6D) directs program logic flow to step 352, wherein Options screen 354 is displayed. Referring to FIG. 11, Options screen 354 includes window 356, OK selection 358, and Cancel selection 360. Window 356 includes Clear MDLink Options Card selection 362, Select ComPort selection 364, and Establish ComSpeed selection 366. In step 368 the operator selects one of options 362–366 and actuates OK selection 358. Step 370 determines whether selection 362 was selected. If so, step 372 displays Card Status screen 340 (FIG. 12). In step 386 a Card Status Selection is made wherein the operator selects one of selections 344–345 and selects OK selection 342. Step 388 determines whether a valid card is present in the selected socket. If so, step 390 displays an "Are You Sure?" screen (not shown). The operator then indicates yes or no in response to the screen displayed in step 390. Step 392 then determines whether the response to the "Are You Sure?" screen was "Yes" or "No". If the response was "Yes", the card is erased in step 394. Step 396 then determines whether the erase attempted in step 394 was successful. If the erase was successful, program logic routes back to Main Screen 230. If the erase was not successful, step 398 displays Unsuccessful Erase Dialogue (not shown), then directs program flow to Main Screen 230.

If the response to step 390 was no, step 392 directs program flow directly to Main Screen 230. If step 388 determines that a valid card was not present in the appropriate socket, step 400 displays Invalid/No Card dialogue (not shown) and directs program flow to Main Screen 230.

Figure 13:
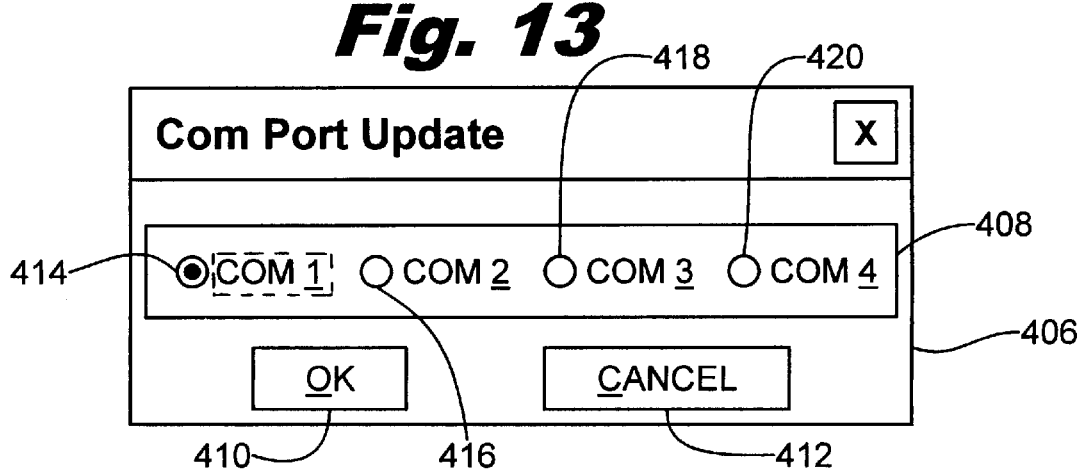
FIG. 13 depicts the Corn Port Update Screen Display generated by the program of the present invention.

Referring again to FIG. 6D, if Select ComPort selection 364 was selected in step 368, step 402 directs logic flow to step 404. In step 404, ComPort Update screen 406 (FIG. 13) is depicted. ComPort Update screen 406 includes window 408, OK selection 410, and Cancel selection 412. Window 408 includes Com 1–Com 4 selection 414–420. In step 404, one of ComPorts 1–4 is selected and OK selection 410 is actuated. The ComPort in use is changed in step 422. A ComPort Update Dialogue (not shown) is depicted in step 424 and program flow is then directed to Main Screen 230.

If Establish ComSpeed Selection 366 was selected in step 368 (FIG. 6D), step 430 directs logic flow to step 432. In step 432, a protocol to automatically establish a compatible data transferal speed is invoked. In step 434, it is determined whether communications have been established at the speed determined in step 432. If communications have been established, logic flow directs to Main Screen 230. If communications have not been established in step 434, an Unsuccessful Communications Dialogue (not shown) is depicted in step 436 and logic flow is then directed to Main Screen 230.

Figures 2, 6E:
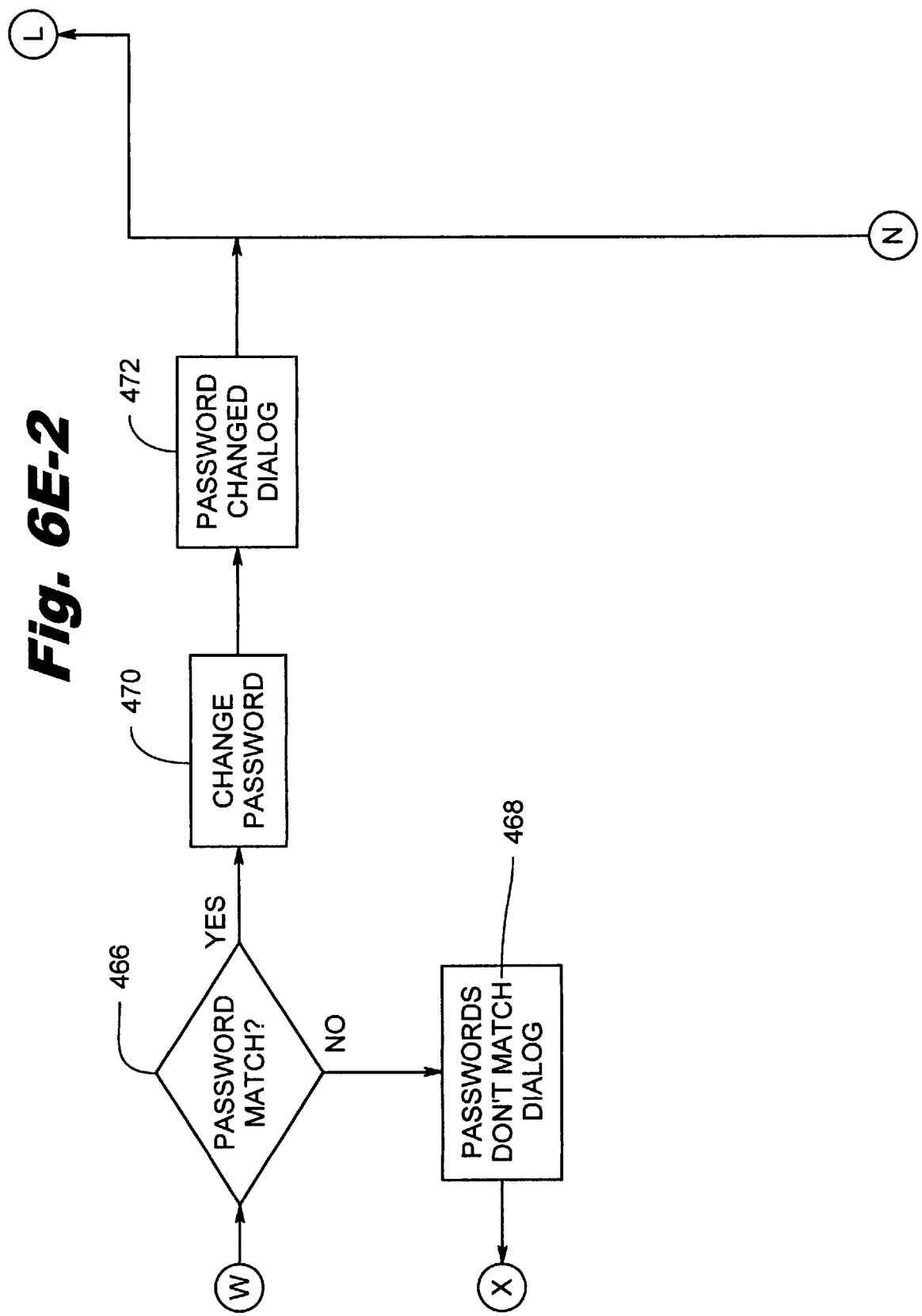
Figure 14:
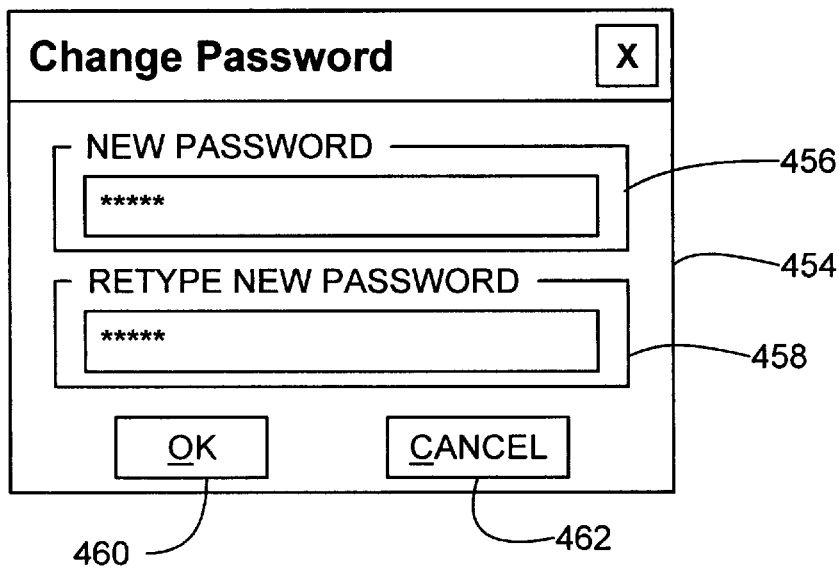
FIG. 14 depicts the Change Password Screen Display generated by the program of the present invention.

Referring to FIG. 6E, if Password selection 254 of Main Screen 230 was selected in step 266, step 450 directs logic flow to step 452. In step 252 Change Password screen 454 (FIG. 14) is displayed. Change Password screen 454 includes New Password window 456, Retype New Password window 458, OK selection 460, and Cancel selection 462. In step 464, the operator keys in a new password character string in window 456, re-keys the new password in window 458, and selects OK selection 460. In step 466, the character strings typed into windows 456–458 are compared. If the character strings in windows 456–458 are not identical, "Passwords Don't Match" dialog (not shown) is depicted in step 468 and logic returns to step 452 for correct password entry in step 464. If the character strings input in windows 456–458 are identical, step 466 directs logic flow to step 470. In step 470, the character string input in windows 456–458 replace the old password in memory resident in PC 105. In step 472, "Password Changed" dialog (not shown) is displayed and program logic routes to Main Screen 230.

Figures 1, 6F:
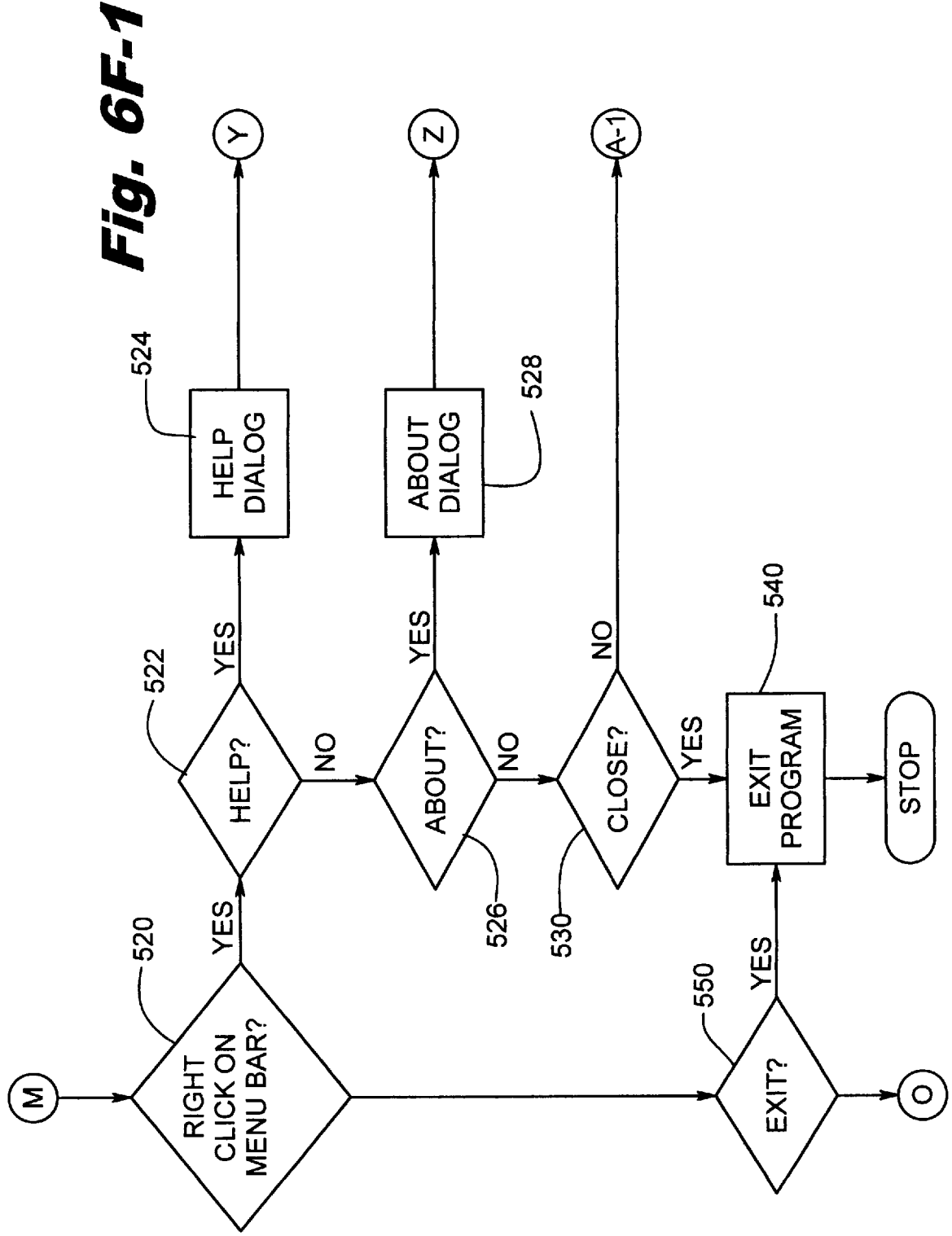
Figures 1, 6G:
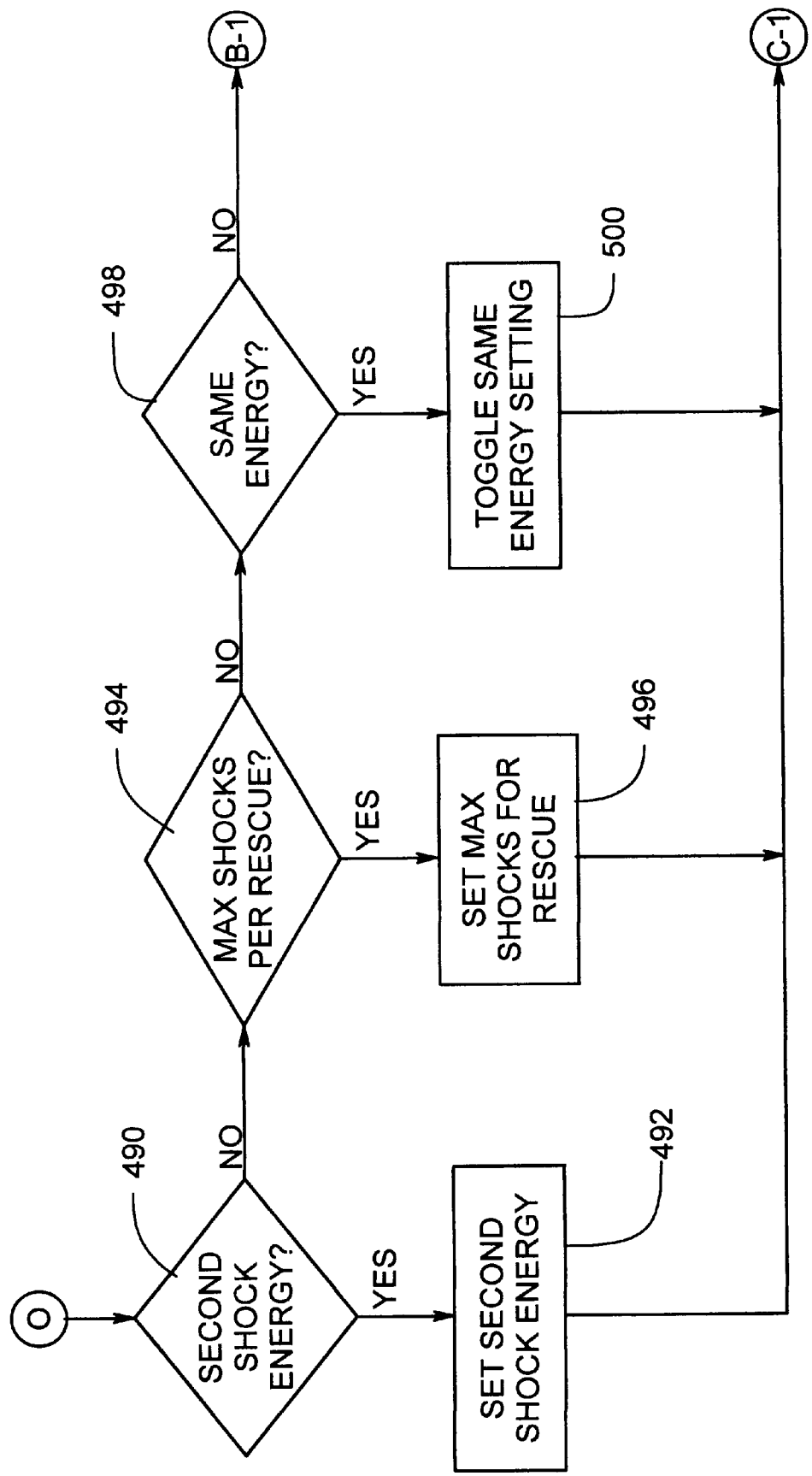
Figures 2, 6G:
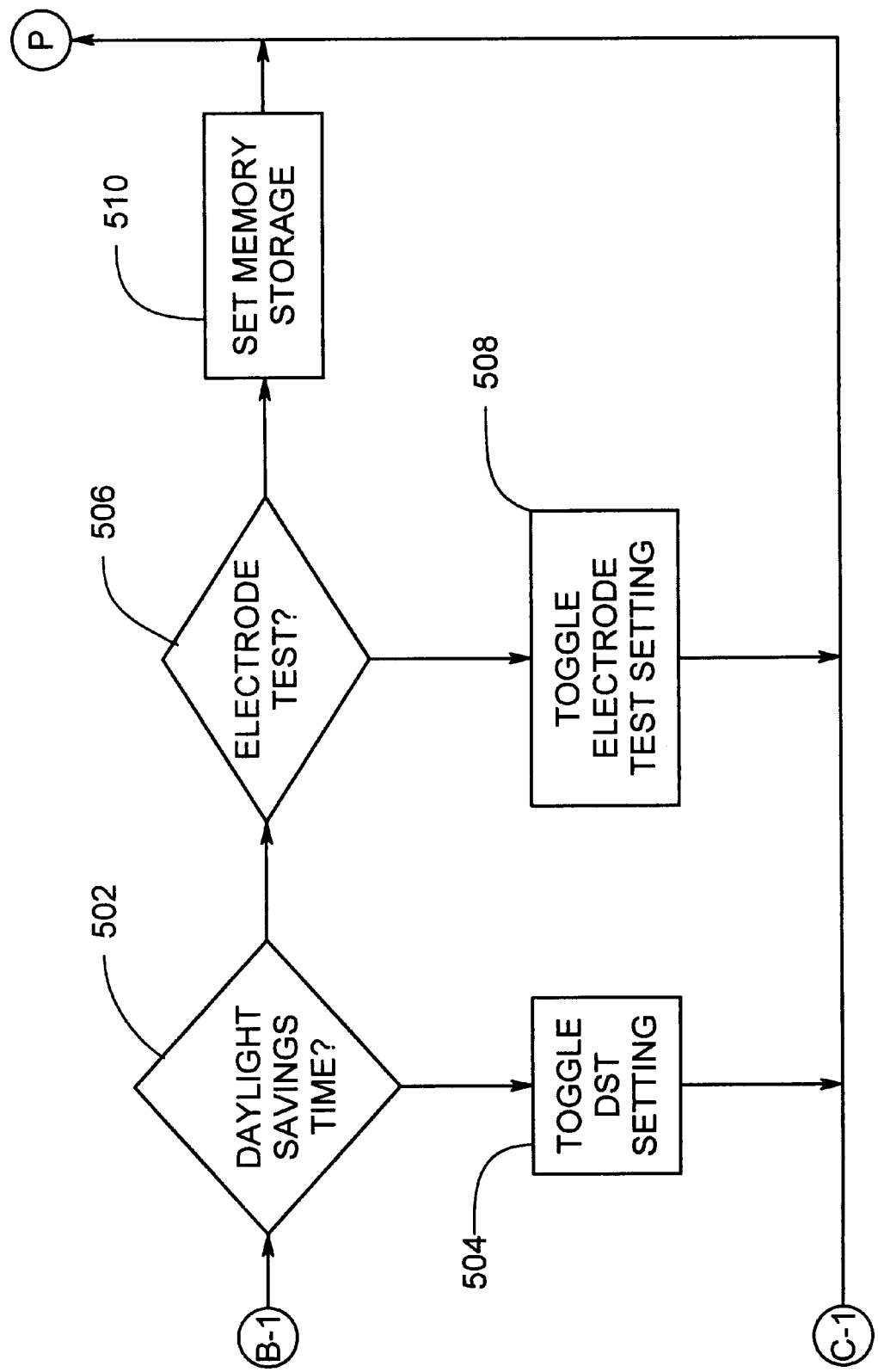

Referring to FIGS. 9 and 6G when parameter settings in windows 232–242 of Main Screen 230 are changed, step 490 determines whether the parameter Second Shock Energy value has been changed. If so, Second Shock Energy Selection, either 200 J or 300 J in either of selections 258–260 is set. If Second Shock Energy Selection in window 232 has not been changed, step 490 directs logic flow to step 494. In step 494, it is determined whether the value for the Maximum Shocks Per Rescue parameter has been altered in window 234 of Main Screen 230. If so, the new value is set in step 496. If step 494 determines that the Maximum Shocks Per Rescue parameter value has not been altered, logic flow is directed to step 498. In step 498, it is determined whether or not the Same Energy After Conversion parameter value of window 236 has been altered. If so, the new setting in window 236 is toggled in step 500. If step 498 determines that the Same Energy After Conversion parameter setting has not been altered, logic is directed to step 502. In step 502, whether the Daylight Savings (DST) parameter setting in window 238 has been changed is determined. If the Daylight Savings parameter setting in window 238 has been changed, step 504 toggles the DST setting. If step 502 determines that the Daylight Savings parameter setting has not been changed, logic is directed to step 506. In step 506, it is determined whether an electrode test will occur during one of the self-tests discussed above. If the setting in window 240 has been altered, the Electrode Test parameter setting is toggled in step 508. If step 506 determines that the Electrode Test parameter setting has not been altered, the setting in External Memory Storage window 242 is input into memory in step 510. In step 510, Long Rescue Selection 262 or Voice Record 264 have been selected and are input into memory. After step 510, logic is directed to Main Screen 230. Also after steps 492, 496, 500, 504, and 508, logic is directed to Main Screen 230 as well.

Referring to FIGS. 9 and 6F Step 520 determines whether a right click on the Menu Bar of Main Screen 230 has occurred in step 266. If so, step 522 determines whether "Help" has been selected. If Help has been selected, Help dialogue (not shown) is displayed in step 524. After Help Dialogue has been displayed, logic directs to Main Screen 230. If step 522 determines that Help has not been selected, step 526 determines whether "About" has been selected. If About has been selected, step 526 directs logic to step 528. In step 528, About dialogue (not shown) is displayed and logic is directed to Main Screen 230. If step 526 determines that About has not been selected, step 530 determines whether "Close" has been selected. If Close has not been selected, logic returns to Main Screen 230. If Close has been selected, the program is exited in step 540.

If step 520 determines that a right click on the Menu Bar has not occurred, step 550 determines whether Exit button 256 of Main Screen 230 has been actuated in step 266. If so, logic routes to step 540 and the program is exited.

A specific data card 29 may be used to change the language that the voice prompts of the AED 10 are delivered in to the operator. The data card 29 contains the program material necessary to convert the language of the voice prompts from the English language prompts that are initially stored in the program memory 76 to, for example, Japanese language prompts. An advantage of this capability is that this update may be readily made in the field, without the need to remove the AED 10 from service and return it to the factory for update.

Further, a specific data card 29 may be used to update or change the software program that is initially stored in program memory 76. Over the service life of a specific AED 10, there may be instances when an improved software program may be desired to be installed in the program memory 76. Being able to update the AED 10 in the field by means of a data card 29, ensures that all AED's 10 are readily configured with the latest software program improvements without being removed from service in order for the update to be installed.

Data card 29 may be used to transfer the selected parameter options to the AED 10 for the automatic reprogramming thereof. Data card 29 is inserted into data card slot 24, as depicted in FIG. 4. Lid 27 is then opened to activate the lid switch 90. The battery status indicators 38 then commence a rapid sequencing up and down through a scale of battery charge indicators. The rapid sequencing occurs while the AED 10 is self-testing. This rapid sequencing is an indication to the operator to press and hold the rescue/resume button 18. A voice prompt "Program mode" is announced to the operator when the AED 10 commences storing the selected parameters on the data card 29. When the prompt "Program mode" is heard by the operator, the rescue/resume button 18 may be released by the operator. When the selected parameters have been successfully transferred to program memory 76 of the AED 10, the voice prompt "Card full. Storing internally" is announced to the operator. The operator may then close the lid 27 to deactivate the lid switch 90 and remove the data card 29 from the AED 10. The program memory 76 is then updated with the input from the data card 29. It should be noted that the parameter changes available through MDLink™, the voice prompt language changes, and the program updates or changes may also be made by direct interaction with the PC 105. AED 10 must be electrically connected to the PC 105 via serial communications cable 112, as depicted in FIG. 4, in order to effect the desired changes directly through interaction with the PC 105.

Because numerous modifications may be made of this invention without departing from the spirit thereof, the scope of the invention is not to be limited to the embodiments illustrated and described. Rather, the scope of the invention is to be determined by appended claims and their equivalents.

What is claimed is:

1. A method of monitoring and altering an operating parameter of an automated external defibrillator (AED) in the field, the AED being designed for performing a rescue intervention on a patient and having a case for housing a power supply, the power supply being electrically connected to a microprocessor and a circuit for generating a defibrillation pulse, the circuit being electrically connectable to a pair of electrodes that are applied to the patient to deliver the defibrillation pulse to the patient, the AED further having an internal program memory and a circuitry to monitor the patient's heart rhythm to determine whether the patient's heart is undergoing a shockable rhythm, said internal program memory and said circuitry to monitor the patient's heart rhythm in electrical communication with the microprocessor, the method comprising:

communicatively coupling an exterior computer comprising an information storage medium to the microprocessor of the AED in the field, the computer and the information storage medium being disposed operationally exterior to said case and being selectively communicatively couplable to the microprocessor of the AED;

initiating a program installed in the information storage medium;

monitoring the operating parameter stored in a microprocessor program; and altering the operating parameter as desired.

2. The method of claim 1 wherein the information storage medium is a personal computer.

3. The method of claim 1 wherein the information storage medium is a data card.

4. The method of claim 1, wherein the step of altering the operating parameter includes altering a second shock energy valve; selecting a maximum number of shocks per rescue; selecting an energy level for a second shock to be delivered to the patient's heart, selecting the energy level of a shock to be delivered in the event that the patient's heart ceasing to fibrillate then reverts to a shockable rhythm between shocks; selecting a setting of an AED clock; and any combination thereof.

5. The method of claim 1, further including the step of performing an electrode test during a self-test.

6. The method of claim 1, further including the step of selecting whether ambient sound will be recorded during the patient intervention.

7. The method of claim 1, further including the step of storing a value for the operating parameter in the internal program memory.

8. The method of claim 7, wherein said storing step further includes storing the operating parameter value in a storage medium device, the storage medium device being external to the AED.

9. The method of claim 1, wherein the step of altering the operating parameter includes selecting a second shock energy value from the group consisting of 300 J and 200 J.

10. The method of claim 1, wherein the step of altering the operating parameter includes selecting a maximum number of shocks per rescue between about 6 and 255.

11. The method of claim 1, wherein the step of altering the operating parameter includes delivering the same energy after the patient converts to a shockable rhythm as was delivered prior to the conversion.

12. An automated external defibrillator (AED) for delivering defibrillation shocks to a patient, comprising:

a power source;

a processor connected to the power source;

a power generation circuit connected to the power source and the processor and including a high voltage generation circuit;

an electrode connector in electrical communication with the power generation circuit and configured to be connected to a plurality of electrodes for conductive engagement with the patient;

patient monitoring circuitry in electrical communication with the electrode connector and the processor;

a program memory connected to the processor and including at least one alterable AED operating parameter; and connecting means to an exterior information storage medium, the external storage medium configured to include said at least one alterable AED operating parameter, said alterable AED operating parameter being altered by implementing software installed in an external computer, said connecting means including a port configured for connecting the external computer to the processor.

13. The AED of claim 12, wherein said connecting means includes a card reader configured to be communicatively coupled to the processor, the card reader accommodating a card with said alterable AED parameter altered by the implementing software and the external computer.

14. The AED of claim 12, further comprising electrode testing circuitry configured to be communicatively coupled to the electrode connector and the processor.

15. The AED of claim 12, wherein said alterable AED operating parameter is selected from the group consisting of a subsequent defibrillation shock energy value for use after delivery of a first defibrillation shock, a maximum number of defibrillation shocks deliverable per rescue, a defibrillation shock energy value subsequent to a defibrillation conversion, an automatic adjustment of an AED time clock, an electrode test, an external memory storage time length, or any combination thereof.

16. The AED of claim 12, wherein said alterable AED operating parameter includes a subsequent defibrillation shock energy value for use after delivery of a first defibrillation shock.

17. The AED of claim 12, wherein said alterable AED operating parameter includes a maximum number of defibrillation shocks deliverable per rescue.

18. The AED of claim 12, wherein said alterable AED operating parameter includes a defibrillation shock energy value subsequent to a defibrillation conversion.

19. An automated external defibrillator (AED) for delivering defibrillation shocks to a patient, comprising:

a power source;

a processor connected to the power source;

a power generation circuit connected to the power source and the processor and including a high voltage generation circuit;

an electrode connector in electrical communication with the power generation circuit and configured to be connected to a plurality of electrodes for conductive engagement with the patient;

patient monitoring circuitry in electrical communication with the electrode connector and the processor;

a program memory connected to the processor and including at least one alterable AED operating parameter;

a real time clock communicatively coupled to the processor; and connecting means to an exterior information storage medium, the external storage medium configured to include said at least one alterable AED operating parameter, said alterable AED operating parameter being altered by implementing software installed in an external computer, said connecting means including a port configured for connecting the real time clock to the external computer.

20. An automated external defibrillator (AED) for delivering defibrillation shocks to a patient, comprising:

a power source;

a processor connected to the power source;

a power generation circuit connected to the power source and the processor and including a high voltage generation circuit;

an electrode connector in electrical communication with the power generation circuit and configured to be connected to a plurality of electrodes for conductive engagement with the patient;

patient monitoring circuitry in electrical communication with the electrode connector and the processor;

a program memory connected to the processor and including at least one alterable AED operating parameter; and connecting means to an exterior information storage medium, the external storage medium configured to include said at least one alterable AED operating parameter, said alterable AED operating parameter being altered by implementing software installed in an external computer, said alterable AED operating parameter including an automatic adjustment of an AED time clock.

21. An automated external defibrillator (AED) for delivering defibrillation shocks to a patient, comprising:

a power source;

a processor connected to the power source;

a power generation circuit connected to the power source and the processor and including a high voltage generation circuit;

an electrode connector in electrical communication with the power generation circuit and configured to be connected to a plurality of electrodes for conductive engagement with the patient;

patient monitoring circuitry in electrical communication with the electrode connector and the processor;

a program memory connected to the processor and including at least one alterable AED operating parameter; and connecting means to an exterior information storage medium, the external storage medium configured to include said at least one alterable AED operating parameter, said alterable AED operating parameter being altered by implementing software installed in an external computer said alterable AED operating parameter including an external memory storage time length.

* * * * *